US011590213B2

(12) United States Patent
Cantor et al.

(10) Patent No.: US 11,590,213 B2
(45) Date of Patent: Feb. 28, 2023

(54) TARGETED EXPANSION OF QA-1-PEPTIDE-SPECIFIC REGULATORY CD8 T CELLS TO AMELIORATE ARTHRITIS

(71) Applicant: Dana-Farber Cancer Institute, Inc., Boston, MA (US)

(72) Inventors: Harvey Cantor, Boston, MA (US); Hye-Jung Kim, Brookline, MA (US); Jianmei Wu Leavenworth, Hoover, AL (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 134 days.

(21) Appl. No.: 16/719,814

(22) Filed: Dec. 18, 2019

(65) Prior Publication Data

US 2020/0297828 A1 Sep. 24, 2020
US 2021/0268081 A9 Sep. 2, 2021

Related U.S. Application Data

(63) Continuation of application No. 14/431,113, filed as application No. PCT/US2013/061851 on Sep. 26, 2013, now Pat. No. 10,548,957.

(60) Provisional application No. 61/773,959, filed on Mar. 7, 2013, provisional application No. 61/707,357, filed on Sep. 28, 2012.

(51) Int. Cl.
| | | |
|---|---|---|
| *A61K 39/00* | (2006.01) | |
| *A61K 35/17* | (2015.01) | |
| *C07K 14/47* | (2006.01) | |
| *C07K 14/74* | (2006.01) | |
| *C12N 5/0783* | (2010.01) | |

(52) U.S. Cl.
CPC .......... *A61K 39/0008* (2013.01); *A61K 35/17* (2013.01); *C07K 14/47* (2013.01); *C07K 14/70539* (2013.01); *C12N 5/0636* (2013.01); *A61K 2039/5154* (2013.01); *A61K 2039/5158* (2013.01); *A61K 2039/55555* (2013.01); *A61K 2039/58* (2013.01); *C12N 2501/2315* (2013.01)

(58) Field of Classification Search
CPC ................ A61K 39/0008; A61K 35/17; A61K 2039/5154; A61K 2039/5158; A61K 2039/55555; A61K 2039/58; C07K 14/47; C07K 14/70539; C12N 5/0636; C12N 2501/2315
See application file for complete search history.

(56) References Cited

U.S. PATENT DOCUMENTS

| | | |
|---|---|---|
| 5,552,303 A | 9/1996 | Grabstein et al. |
| 6,780,843 B2 | 8/2004 | Lin et al. |
| 8,709,424 B2 | 4/2014 | Schebye et al. |
| 9,783,846 B2 | 10/2017 | Olek |
| 10,548,957 B2 | 2/2020 | Cantor et al. |
| 10,596,195 B2 | 3/2020 | Cantor et al. |
| 2002/0022030 A1 | 2/2002 | Marrack et al. |
| 2007/0081991 A1* | 4/2007 | Soderstrom ............. A61P 37/02 424/133.1 |
| 2007/0160578 A1 | 7/2007 | Waldmann et al. |
| 2008/0152642 A1 | 6/2008 | Georgopoulos et al. |
| 2009/0155292 A1 | 6/2009 | Santamaria et al. |
| 2009/0238791 A1 | 9/2009 | Jacques et al. |
| 2009/0324538 A1 | 12/2009 | Wong et al. |
| 2010/0260781 A1 | 10/2010 | Murray |
| 2012/0121649 A1* | 5/2012 | Santamaria ............ A61K 47/62 424/277.1 |
| 2013/0157363 A1 | 6/2013 | Kim et al. |
| 2013/0183321 A1 | 7/2013 | Smith et al. |
| 2013/0302276 A1 | 11/2013 | Cantor et al. |
| 2013/0317113 A1 | 11/2013 | Hadlock et al. |
| 2014/0220012 A1 | 8/2014 | Noelle et al. |
| 2014/0335530 A1 | 11/2014 | Drake et al. |
| 2015/0250862 A1 | 9/2015 | Cantor et al. |
| 2017/0224732 A1 | 8/2017 | Cantor et al. |
| 2017/0269076 A1 | 9/2017 | Cantor et al. |
| 2019/0178884 A1 | 6/2019 | Cantor et al. |
| 2019/0192565 A1 | 6/2019 | Cantor et al. |

FOREIGN PATENT DOCUMENTS

| | | | |
|---|---|---|---|
| WO | WO 2006/063974 A2 | 6/2006 | |
| WO | WO 2007/068487 A2 | 6/2007 | |
| WO | WO 2007/110230 A2 | 10/2007 | |
| WO | WO 2007/136518 A2 | 11/2007 | |
| WO | WO 2007/110230 A3 | 12/2007 | |
| WO | WO 2008/101272 A1 | 8/2008 | |
| WO | WO 2008/109852 * | 9/2008 | ............. A61K 39/00 |
| WO | WO 2008/109852 A2 | 9/2008 | |

(Continued)

OTHER PUBLICATIONS

O'Herrin et al. (J. Immunol., 167: 2555-2560, 2001).*
Crew et al. (Molecular Immunology, 42: 1205-1214, 2005).*
Park et al. (Molecular Pharmaceutics, 8(1): 143-152, published online: Oct. 26, 2010).*
Zhang et al. (Immunity, 8: 591-599, 1998).*
U.S. Appl. No. 13/878,894, filed Jun. 26, 2013, Abandoned, 2013-0302276.

(Continued)

*Primary Examiner* — Nelson B Moseley, II
(74) *Attorney, Agent, or Firm* — Baker Donelson

(57) ABSTRACT

Nanoparticles to treat autoimmune diseases and HIV infection are provided. The nanoparticles comprise a biocompatible polymer and a complex, wherein the complex is a major histocompatibility complex (MHC) class I antigen E (HLA-E) linked to a peptide, and wherein the HLA-E-peptide complex is linked to the surface of the nanoparticle. The present invention also relates to methods for treating autoimmune diseases and HIV infection.

15 Claims, 4 Drawing Sheets

Specification includes a Sequence Listing.

(56) References Cited

FOREIGN PATENT DOCUMENTS

| WO | WO 2009/002562 A2 | 12/2008 |
|---|---|---|
| WO | WO 2009/027284 A1 | 3/2009 |
| WO | WO 2010/071836 A1 | 6/2010 |
| WO | WO 2012/054509 A2 | 4/2012 |
| WO | WO 2012/079000 A1 | 6/2012 |
| WO | WO 2014/039513 A2 | 3/2014 |
| WO | WO 2014/052454 A2 | 4/2014 |
| WO | WO 2014/058915 A2 | 4/2014 |
| WO | WO 2014/183056 A1 | 11/2014 |
| WO | WO 2014/039513 A3 | 7/2015 |

OTHER PUBLICATIONS

U.S. Appl. No. 15/405,434, filed Jan. 13, 2017, Granted, U.S. Pat. No. 10,596,195.
U.S. Appl. No. 14/431,113, filed Mar. 25, 2015, Granted, U.S. Pat. No. 10,548,957.
U.S. Appl. No. 15/506,868, filed Feb. 27, 2017, Abandoned, 2017-0269076.
U.S. Appl. No. 16/195,586, filed Nov. 19, 2018, Published, 2019-0178884.
U.S. Appl. No. 15/578,871, filed Dec. 1, 2017, Published, 2019-0192565.
EP11835009.9, Jan. 12, 2015, Partial Supplementary European Search Report.
EP11835009.9, May 13, 2015, Extended European Search Report.
EP11835009.9, Jun. 19, 2015, Corrected European Search Opinion.
PCT/US2011/056746, Feb. 21, 2012, Invitation to Pay Additional Fees.
PCT/US2011/056746, May 1, 2012, International Search Report and Written Opinion.
PCT/US2011/056746, May 2, 2013, International Preliminary Report on Patentability.
PCT/US2013/061851, Jan. 31, 2014, Invitation to Pay Additional Fees.
PCT/US2013/061851, Apr. 10, 2014, International Search Report and Written Opinion.
PCT/US2013/061851, Jun. 25, 2015, International Preliminary Report on Patentability.
EP 15836839.9, Jan. 11, 2018, Partial Supplementary European Search Report.
EP 15836839.9, Apr. 11, 2018, Extended European Search Report.
PCT/US2015/047189, Feb. 2, 2016, International Search Report and the Written Opinion.
PCT/US2015/047189, Mar. 9, 2017, International Preliminary Report on Patentability.
EP1680451.4, Dec. 20, 2018, Extended European Search Report.
PCT/US2016/035692, Sep. 13, 2016, International Search Report and Written Opinion.
PCT/US2016/035692, Dec. 14, 2017, International Preliminary Report on Patentability.
Partial Supplementary European Search Report for EP11835009.9 dated Jan. 12, 2015.
Extended European Search Report for EP11835009.9 dated May 13, 2015.
Corrected European Search Opinion for EP11835009.9 dated Jun. 19, 2015.
Invitation to Pay Additional Fees for PCT/US2011/056746 dated Feb. 21, 2012.
International Search Report and Written Opinion for PCT/US2011/056746 dated May 1, 2012.
International Preliminary Report on Patentability for PCT/US2011/056746 dated May 2, 2013.
Invitation to Pay Additional Fees for PCT/US2013/61851 dated Jan. 31, 2014.
International Search Report and Written Opinion for PCT/US2013/61851 dated Apr. 10, 2014.
International Preliminary Report on Patentability for PCT/US2013/061851 dated Jun. 25, 2015.
Partial Supplementary European Search Report for EP 15836839.9 dated Jan. 11, 2018.
Extended European Search Report for Application No. EP 15836839.9 dated Apr. 11, 2018.
International Search Report and Written Opinion for PCT/US2015/047189 dated Feb. 2, 2016.
International Preliminary Report on Patentability for PCT/US2015/047189 dated Mar. 9, 2017.
Extended European Search Report for Application No. EP1680451.4 dated Dec. 20, 2018.
International Search Report and Written Opinion for PCT/US2016/035692 dated Sep. 13, 2016.
International Preliminary Report on Patentability for PCT/US2016/035692 dated Dec. 14, 2017.
[No Author Listed], Antibodies: A Laboratory Manual, Harlow and Lane, Cold Spring Harbor Laboratory, New York. 1988.
[No Author Listed], Peripheral blood mononuclear cell From Wikipedia, the free encyclopedia; pp. 1-2 downloaded on Jul. 13, 2018.
Almeida et al., Competition controls the rate of transition between the peripheral pools of CD4+CD25− and CD4+CD25+ T cells. Int Immunol. Nov. 2006;18(11):1607-13. Epub Sep. 20, 2006.
Alvarez et al., Disruption of CD8+ Treg activity results in expansion of T follicular helper cells and enhanced antitumor immunity. Cancer Immunol Res. Mar. 2014;2(3):207-16. doi: 10.1158/2326-6066.CIR-13-0121. Epub Dec. 31, 2013.
Anderton et al., Negative selection during the peripheral immune response to antigen. J Exp Med. Jan. 1, 2001;193(1):1-11.
Anfossi et al., Biology of T memory type 1 cells. Immunol Rev. Jun. 2001;181:269-78.
Anfossi et al., Expansion and function of CD8+ T cells expressing Ly49 inhibitory receptors specific for MHC class I molecules. J Immunol. Sep. 15, 2004;173(6):3773-82.
Aoki et al., Fluorescence resonance energy transfer imaging of cell signaling from in vitro to in vivo: basis of biosensor construction, live imaging, and image processing. Dev Growth Differ. May 2013;55(4):515-22. doi:10.1111/dgd.12039. Epub Feb. 7, 2013.
Arai et al., Extensive use of FRET in biological imaging. Microscopy (Oxf). Aug. 2013;62(4):419-28.
Aramburu et al., Affinity-driven peptide selection of an NFAT inhibitor more selective than cyclosporin A. Science. Sep. 24, 1999;285(5436):2129-33.
Arvey et al., Inflammation-induced repression of chromatin bound by the transcription factor Foxp3 in regulatory T cells. Nat Immunol. Jun. 2014;15(6):580-7. doi: 10.1038/ni.2868. Epub Apr. 13, 2014.
Ashkar et al., Eta-1 (osteopontin): an early component of type-1 (cell-mediated) immunity. Science. Feb. 4, 2000;287(5454):860-4.
Baine et al., Helios induces epigenetic silencing of IL2 gene expression in regulatory T cells. J Immunol. Feb. 1, 2013;190(3):1008-16. doi: 10.4049/jimmunol.1200792. Epub Dec. 28, 2012.
Baumeister et al., Coinhibitory Pathways in Immunotherapy for Cancer.Annu Rev Immunol. May 20, 2016;34:539-73. doi: 10.1146/annurev-immunol-032414-112049. Epub Feb. 25, 2016.
Baumjohann et al., Identification of T follicular helper (Tfh) cells by flow cytometry. Protocal Exchange. Jun. 18, 2013.
Baumjohann et al., Cutting Edge: Distinct waves of BCL6 expression during T follicular helper cell development. J Immunol. Sep. 1, 2011;187(5):2089-92. doi: 10.4049/jimmunol.1101393. Epub Jul. 29, 2011.
Beerens et al., Protein transduction domains and their utility in gene therapy. Curr Gene Ther. Oct. 2003;3(5):486-94.
Bernard et al., Identification of an interleukin-15alpha receptor-binding site on human interleukin-15. J Biol Chem. Jun. 4, 2004;279(23):24313-22. Epub Mar. 23, 2004.
Beyer et al., Regulatory T cells in cancer. Blood. Aug. 1, 2006;108(3):804-11.
Bindea et al., Spatiotemporal dynamics of intratumoral immune cells reveal the immune landscape in human cancer. Immunity. Oct. 17, 2013;39(4):782-95. doi: 10.1016/j.immuni.2013.10.003.
Blackburn et al., Selective expansion of a subset of exhausted CD8 T cells by alphaPD-L1 blockade. Proc Natl Acad Sci U S A. Sep. 30, 2008;105(39):15016-21. doi: 10.1073/pnas.0801497105. Epub Sep. 22, 2008.

(56) References Cited

OTHER PUBLICATIONS

Bouneaud et al., Impact of negative selection on the T cell repertoire reactive to a self-peptide: a large fraction of T cell clones escapes clonal deletion. Immunity. Dec. 2000;13(6):829-40.
Broomé et al., Primary sclerosing cholangitis, inflammatory bowel disease, and colon cancer. Semin Liver Dis. Feb. 2006;26(1):31-41.
Buback et al., Osteopontin and the skin: multiple emerging roles in cutaneous biology and pathology. Exper. Dermatol. 2009;18:750-759.
Bubier et al., Treatment of BXSB-Yaa mice with IL-21R-Fc fusion protein minimally attenuates systemic lupus erythematosus. Ann N Y Acad Sci. Sep. 2007:1110:590-601.
Bunting et al., New effector functions and regulatory mechanisms of BCL6 in normal and malignant lymphocytes. Curr Opin Immunol. Jun. 2013;25(3):339-46. Doi:10.1016/j.coi.2013.05.003. Epub May 30, 2013.
Buommino et al., Osteopontin: a new emerging role in psoriasis. Arch. Dermatol. Res. 2009;301:397-404.
Burchill et al., Distinct effects of STAT5 activation on CD4+ and CD8+ T cell homeostasis: development of CD4+CD25+ regulatory T cells versus CD8+ memory T cells. J Immunol. Dec. 1, 2003;171(11):5853-64.
Burchill et al., IL-2 receptor beta-dependent STAT5 activation is required for the development of Foxp3+ regulatory T cells. J Immunol. Jan. 1, 2007;178(1):280-90.
Burchill et al., Linked T cell receptor and cytokine signaling govern the development of the regulatory T cell repertoire. Immunity. Jan. 2008;28(1):112-21. doi: 10.1016/j.immuni.2007.11.022.
Cai et al., Helios deficiency has minimal impact on T cell development and function. J Immunol. Aug. 15, 2009;183(4):2303-11. doi: 10.4049/jimmunol.0901407. Epub Jul. 20, 2009.
Cantor et al., Regulation of T-helper-cell lineage development by osteopontin: the inside story. Nat Rev Immunol. Feb. 2009;9(2):137-41. Doi:10.1038/nri2460.
Cantor, Definition of a Sublineage of CD8 Cells Programmed to Exert Regulatory Activity: CD8+ Treg. Presentation given on Jun. 14, 2009. FOCIS Meeting, San Francisco CA. 5 Pages.
Cantor, Definition of a Sublineage of CD8 Cells Programmed to Exert Regulatory Activity: CD8+ Treg. Presentation given on Sep. 4, 2009. Pasteur Institute, Paris, FR. 7 Pages.
Cantor, Definition of a Sublineage of CD8 Cells Programmed to Maintain Self Tolerance: CD8+ Treg. Presentation given on Nov. 2, 2009. Northwestern, Chicago IL. 7 Pages.
Cantor, Development of T cell subsets and self-tolerance. Presentation given on Dec. 2, 2008. PARC/ Ragon Institute, Cambridge, MA. 12 Pages.
Cantor, Regulation of follicular helper cells by Opn+ dendritic cells and CD8+ regulatory cells. Presentation given on Aug. 2, 2010. FASEB Summer Conference, Steamboat Springs, CO. 49 Pages.
Cantor, Suppressor cells revisited: CD8+ Treg. Presentation given on Aug. 30, 2009. ESOT, Paris, FR. 7 Pages.
Cantor, Therapeutic use of anti-NKG2A F(ab)2 in the context of EAE/MS and RA. Therapeutic manipulation of CD8+ Treg in the context of SLE. Presentation given on Nov. 12, 2009. Copenhagen, DK. 91 Pages.
Carbone et al., Report of the Committee on Hodgkin's Disease Staging Classification. Cancer Res. Nov. 1971;31(11):1860-1.
Cerchietti et al., A purine scaffold Hsp90 inhibitor destabilizes BCL-6 and has specific antitumor activity in BCL-6-dependent B cell lymphomas. Nat Med. Dec. 2009;15(12):1369-76. Doi: 10.1038/nm.2059. Epub Nov. 22, 2009.
Chagan-Yasutan et al., Involvement of osteopontin and its signaling molecule CD44 in clinicopathological features of adult T cell leukemia. Leukemia Res. May 9, 2011;35(11):1484-90.
Chang et al., TRAF3 regulates the effector function of regulatory T cells and humoral immune responses. J Exp Med. Jan. 13, 2014;211(1):137-51. Doi:10.1084/jem.20131019. Epub Dec. 30, 2013.

Chauvin et al., TIGIT and PD-1 impair tumor antigen-specific CD8+ T cells in melanoma patients J Clin Invest. May 2015;125(5):2046-58. doi: 10.1172/JCI80445. Epub Apr. 13, 2015.
Chen et al., Elevated plasma osteopontin level is associated with occurrence of psoriasis and is an unfavorable cardiovascular risk factor in patients with psoriasis. J Am Acad Dermatol. Feb. 2009;60(2):225-30. Doi: 10.1016/j.jaad.2008.09.046. Epub Nov. 25, 2008.
Chen et al., Preferential development of CD4 and CD8 T regulatory cells in RasGRP1-deficient mice. J Immunol. May 1, 2008;180(9):5973-82.
Chen et al., Regulatory T cell clones induced by oral tolerance: suppression of autoimmune encephalomyelitis. Science. Aug. 26, 1994;265(5176):1237-40.
Choi et al., Cutting edge: STAT1 is required for IL-6-mediated Bcl6 induction for early follicular helper cell differentiation. J Immunol. Apr. 1, 2013;190(7):3049-53. Doi: 10.4049/jimmunol.1203032. Epub Feb. 27, 2013.
Choi et al., ICOS receptor instructs T follicular helper cell versus effector cell differentiation via induction of the transcriptional repressor Bcl6. Immunity. Jun. 24, 2011;34(6):932-46. Doi: 10.1016/j.immuni.2011.03.023.
Chung et al., Follicular regulatory T (Tfr) cells with dual Foxp3 and Bcl6 expression suppress germinal center reactions. Nat Med. Jul. 24, 2011;17(8):983-8. Doi: 10.1038/nm.2426.
Chwae et al., Molecular mechanism of the activation-induced cell death inhibition mediated by a p70 inhibitory killer cell Ig-like receptor in Jurkat T cells. J Immunol. Oct. 1, 2002;169(7):3726-35.
Coles et al., Memory CD8 T lymphocytes express inhibitory MHC-speciftc Ly49 receptors. Eur J Immunol. Jan. 2000;30(1):236-44.
Compston et al., Multiple sclerosis. Lancet. Oct. 25, 2008;372(9648):1502-17. Doi: 10.1016/S0140-6736(08)61620-7.
Coussens et al., Inflammation and cancer. Nature. Dec. 19-26, 2002;420(6917):860-7.
Crew et al., An HLA-E single chain trimer inhibits human NK cell reactivity towards porcine cells. Mol Immunol. Jun. 2005;42(10):1205-14. Epub Jan. 8, 2005.
Crotty et al., Effectors and memories: Bcl-6 and Blimp-1 in T and B lymphocyte differentiation. Nat Immunol. Feb. 2010;11(2):114-20. Doi: 10.1038/ni.1837. Epub Jan. 19, 2010.
Crotty, Follicular helper CD4 T cells (TFH). Annu Rev Immunol. 2011;29:621-63. Doi: 10.1146/annurev-immunol-031210-101400.
Curiel et al., Specific recruitment of regulatory T cells in ovarian carcinoma fosters immune privilege and predicts reduced survival. Nat Med. Sep. 2004;10(9):942-9. Epub Aug. 22, 2004.
D'Andrea et al., Regulation of T cell lymphokine production by killer cell inhibitory receptor recognition of self HLA class I alleles. J Exp Med. Aug. 1, 1996;184(2):789-94.
Davies et al., A peptide from heat shock protein 60 is the dominant peptide bound to Qa-1 in the absence of the MHC class la leader sequence peptide Qdm. J Immunol. May 15, 2003;170(10):5027-33.
Deshayes et al., Fluorescence technologies for monitoring interactions between biological molecules in vitro. Prog Mol Biol Transl Sci. 2013;113:109-43. Doi: 10.1016/B978-0-12-386932-6.00004-1.
Diamandis et al., The biotin-(strept)avidin system: principles and applications in biotechnology. Clin Chem. May 1991;37(5):625-36.
Doria et al., Long-term prognosis and causes of death in systemic lupus erythematosus. Am J Med. Aug. 2006;119(8):700-6.
Duk et al., The biotin/avidin-mediated microtiter plate lectin assay with the use of chemically modified glycoprotein ligand. Anal Biochem. Sep. 1994;221(2):266-72.
Feng et al., Control of the inheritance of regulatory T cell identity by a cis element in the Foxp3 locus. Cell. Aug. 14, 2014;158(4):749-63. doi: 10.1016/j.cell.2014.07.031.
Fontenot et al., A function for interleukin 2 in Foxp3-expressing regulatory T cells. Nat Immunol. Nov. 2005;6(11):1142-51. Epub Oct. 16, 2005. Erratum in: Nat Immunol. Apr. 2006;7(4):427.
Franciso et al., PD-L1 regulates the development, maintenance, and function of induced regulatory T cells. J Exp Med. Dec. 21, 2009;206(13):3015-29. doi: 10.1084/jem.20090847. Epub Dec. 14, 2009.

(56) References Cited

OTHER PUBLICATIONS

Fu et al., A multiply redundant genetic switch 'locks in' the transcriptional signature of regulatory T cells. Nat Immunol. Oct. 2012;13(10):972-80. doi: 10.1038/ni.2420. Epub Sep. 9, 2012.

Gandhi et al., Are patients with inflammatory bowel disease at increased risk of coronary artery disease? Am J Med. Oct. 2012;125(10):956-62. Doi: 10.1016/j.amjmed.2012.03.015. Epub Jul. 25, 2012.

Gati et al., CD158 receptor controls cytotoxic T-lymphocyte susceptibility to tumor-mediated activation-induced cell death by interfering with Fas signaling. Cancer Res. Nov. 2003;63(21):7475-82.

Gays et al., Functional analysis of the molecular factors controlling Qa1-mediated protection of target cells from NK lysis. J. Immunol. Mar. 2001;166(3):1601-10.

Gigoux et al., Inducible costimulatory promotes helper T-cell differentiation through phosphoinositide 3-kinase. Proc Natl Acad Sci U S A. Dec. 1, 2009;106(48):20371-6. Doi:10.1073/pnas. 0911573106. Epub Nov. 13, 2009.

Glasmacher et al., Roquin binds inducible ignaling ory Mrna and effectors of Mrna decay to induce microRNA-independent post-transcriptional repression. Nat Immunol. Aug. 2010;11(8):725-33. Doi: 10.1038/ni.1902. Epub Jul. 18, 2010.

Goedhart et al., An introduction to fluorescence imaging techniques geared towards biosensor applications. Methods Mol Biol. 2014;1071:17-28. Doi: 10.1007/978-1-62703-622-1_2.

Goldrath et al., Selecting and maintaining a diverse T-cell repertoire. Nature. Nov. 18, 1999;402(6759):255-62.

Gray et al., The BH3-only proteins Bim and Puma cooperate to impose deletional tolerance of organ-specific antigens. Immunity. Sep. 21, 2012;37(3):451-62. doi: 10.1016/j.immuni.2012.05.030. Epub Sep. 6, 2012.

Groux et al., A CD4+ T-cell subset inhibits antigen-specific T-cell responses and prevents colitis. Nature. Oct. 16, 1997;389(6652):737-42.

Groux et al., Interleukin-10 induces a long-term antigen-specific anergic state in human CD4+ T cells. J Exp Med. Jul. 1, 1996;184(1):19-29.

Haxhinasto et al., The AKT-Mtor axis regulates de novo differentiation of CD4+Foxp3+ cells. J Exp Med. Mar. 17, 2008;205(3):565-74. Doi:10.1084/jem.20071477. Epub Feb. 18, 2008.

Hayashi et al., Germ cell specification in mice. Science. Apr. 20, 2007;316(5823):394-6.

Hedfors et al., Long-term proliferation and survival of in vitro-activated T cells is dependent on Interleukin-2 receptor Signaling but not on the high-affinity IL-2R. Scand J Immunol. Nov. 2003;58(5):522-32.

Hill et al., Foxp3 transcription-factor-dependent and -independent regulation of the regulatory T cell transcriptional signature. Immunity. Nov. 2007;27(5):786-800.

Hirsch et al., Easily reversible desthiobiotin binding to streptavidin, avidin, and other biotin-binding proteins: uses for protein labeling, detection, and isolation. Anal Biochem. Sep. 15, 2002;308(2):343-57.

Hirschhorn-Cymerman et al., Induction of tumoricidal function in CD4+ T cells is associated with concomitant memory and terminally differentiated phenotype. J Exp Med. Oct. 22, 2012;209(11):2113-26. doi: 10.1084/jem.20120532. Epub Sep. 24, 2012.

Hoffmann et al., Isolation of CD4+CD25+ regulatory T cells for clinical trials. Biol Blood Marrow Transplant. Mar. 2006;12(3):267-74.

Hong et al., High-dose cyclophosphamide-mediated anti-tumor effects by the superior expansion of CD44(high) cells after their selective depletion. Immunobiology. Mar. 2010;215(3):182-93. doi: 10.1016/j.imbio.2009.01.010. Epub May 22, 2009.

Horsley et al., Blimp1 defines a progenitor population that governs cellular input to the sebaceous gland. Cell. Aug. 11, 2006;126(3):597-609.

Huang et al., Gene expression profiles in BCL11B-siRNA treated malignant T cells. J. Hermatol Oncol. May 15, 2011;4(1, 23):1-6.

Huang et al., Lineage-specific functions of Bcl-6 in immunity and inflammation are mediated by distinct biochemical mechanisms. Nat Immunol. Apr. 2013;14(4):380-8. Doi: 10.1038/ni.2543. Epub Mar. 3, 2013.

Huff et al., A fluorescent glutathione analog for monitoring interactions of GST fusion proteins. The FASEB Journal. Apr. 2012;26(1):613.6.

Hur et al., Osteopontin-induced relapse and progression of autoimmune brain disease through enhanced survival of activated T cells. Nat Immunol. Jan. 2007;8(1):74-83. Epub Dec. 3, 2006.

Iaffaldano et al., The improvement of cognitive functions is associated with a decrease of plasma Osteopontin levels in Natalizumab treated relapsing multiple sclerosis. Brain Behav Immun. Jan. 2014;35:176-81. Doi: 10.1016/j.bbi.2013.08.009. Epub Aug. 30, 2013.

Inobe et al., IL-4 is a differentiation factor for transforming growth factor-beta secreting Th3 cells and oral administration of IL-4 enhances oral tolerance in experimental allergic encephalomyelitis. Eur J Immunol. Sep. 1998;28(9):2780-90.

Inoue et al., Intracellular osteopontin (iOPN) and immunity. Immunol Res. Apr. 2011;49(1-3):160-72. Doi: 10.1007/s12026-010-8179-5.

Izui et al., The Y chromosome from autoimmune BXSB/MpJ mice induces a lupus-like syndrome in (NZW × C57BL/6)F1 male mice, but not in C57BL/6 male mice. Eur J Immunol. Jun. 1988;18(6):911-5.

Jiang et al. HLA-E-restricted regulatory CD8(+) T cells are involved in development and control of human autoimmune type 1 diabetes. J Clin Invest. Oct. 2010;120(10):3641-50. doi: 10.1172/JCI43522. Epub Sep. 27, 2010.

Jiang et al., Regulatory CD8+ T cells fine-tune the myelin basic protein-reactive T cell receptor V beta repertoire during experimental autoimmune encephalomyelitis. Proc Natl Acad Sci USA. Jul. 8, 2003;100(14):8378-83. Epub Jun. 24, 2003.

Jin et al., Role of PD-1 in regulating T-cell immunity. Curr Top Microbiol Immunol. 2011;350:17-37. doi: 10.1007/82_2010_116.

Johnston et al., Bcl6 and Blimp-1 are reciprocal and antagonistic regulators of T follicular helper cell differentiation. Science. Aug. 21, 2009;325(5943):1006-10. Doi: 10.1126/science.1175870. Epub Jul. 16, 2009.

Judge et al., Interleukin 15 controls both proliferation and survival of a subset of memory-phenotype CD8(+) T cells. J Exp Med. Oct. 7, 2002;196(7):935-46.

June, Principles of adoptive T cell cancer therapy. J Clin Invest. May 2007;117(5):1204-12.

Kaleta, Role of Osteopontin in Systemic Lupus Erythematosus. Arch Immunol. Ther. Exp. 2014;62:475-482.

Kalos et al., Adoptive T cell transfer for cancer immunotherapy in the era of synthetic biology. Immunity. Jul. 25, 2013;39(1):49-60. doi:10.1016/j.immuni.2013.07.002.

Kaluza et al., Improving the outcome of adoptive cell transfer by targeting tumor escape. Oncoimmunollogy. Jan. 2013;2(1):e22059-1-3.

Kang et al., MicroRNAs of the miR-17~92 family are critical regulators of T(FH) differentiation. Nat Immunol. Aug. 2013;14(8):849-57. doi: 10.1038/ni.2648. Epub Jun. 30, 2013.

Karttunen et al., Detection of rare antigen-presenting cells by the lacZ T-cell activation assay suggests an expression cloning strategy for T-cell antigens. Proc Natl Acad Sci U S A. Jul. 1, 1992;89(13):6020-4.

Kearney et al., Visualization of peptide-specific T cell immunity and peripheral tolerance induction in vivo. Immunity. Jul. 1994;1(4):327-39.

Kerfoot et al., Germinal center B cell and T follicular helper cell development initiates in the interfollicular zone. Immunity. Jun. 24, 2011;34(6):947-60. doi:10.1016/j.immuni.2011.03.024.

Keszei et al., Expansion of an osteopontin-expressing T follicular helper cell subset correlates with autoimmunity in B6.Sle 1b mice and is suppressed by the H1-isoform of the Slamf6 receptor. FASEB J. Aug. 2013;27(8):3123-31. doi: 10.1096/fj.12-226951. Epub Apr. 29, 2013.

Kikuchi et al., Differential role of three major New Zealand Black-derived loci linked with Yaa-induced murine lupus nephritis. J Immunol. Jan. 15, 2005;174(2):1111-7.

(56) References Cited

OTHER PUBLICATIONS

Kim et al., CD8+ T regulatory cells express the Ly49 Class I MHC receptor and are defective in autoimmune prone B6-Yaa mice. Proc Natl Acad Sci U S A. Feb. 1, 2011;108(5):2010-5. doi: 10.1073/pnas.1018974108. Epub Jan. 13, 2011.
Kim et al., Inhibition of follicular T-helper cells by CD8(+) regulatory T cells is essential for self tolerance. Nature. Sep. 16, 2010;467(7313):328-32.
Kim et al., Inhibition of follicular T-helper cells by CD8(+) Treg is essential for self tolerance. Nature. Sep. 16, 2010;467(7313):328-32. doi: 10.1038/nature09370.
Kim et al., Regulatory T cells prevent catastrophic autoimmunity throughout the lifespan of mice. Nat Immunol. Feb. 2007;8(2):191-7. Epub Nov. 30, 2006.
Kim et al., Stable inhibitory activity of regulatory T cells requires the transcription factor Helios. Science. Oct. 18, 2015;350(6258):334-9. doi: 10.1126/science.aad0616.
Kim, CD8+ Treg and Autoimmunity. The 4$^{th}$ Symposium of Immunological Self. Division of Immunology Seminar, HMS. Presentation given on Jan. 27, 2012. Kyoto, Japan. 8 Pages.
Kim, Qa-1 restricted CD8+ Treg and Autoimmunity. The 4th Symposium of Immunological Self Division of Immunology Seminar, HMS. Presentation given on Apr. 27, 2012. Division of Immunology Seminar Series, Harvard Medical School, Boston MA. 9 Pages.
Kim, Shaping of antibody responses by CD8+ Regulatory T Cells. The 4$^{th}$ Symposium of Immunological Self. Division of Immunology Seminar, HMS. Presentation given on Nov. 29, 2011. German Rheumatology Research Institute, Berlin, Germany. 9 Pages.
King et al., T follicular helper (TFH) cells in normal and dysregulated immune responses. Annu Rev Immunol. 2008;26:741-66. doi:10.1146/annurev.immunol.26.021607.090344.
Kitagawa et al., Molecular determinants of regulatory T cell development: the essential roles of epigenetic changes. Front Immunol. May 10, 2013;4:106. doi: 10.3389/fimmu.2013.00106. eCollection 2013.
Krönke et al., Lenalidomide causes selective degradation of IKZF1 and IKZF3 in multiple myeloma cells. Science. Jan. 17, 2014;343(6168):301-5. doi: 10.1126/science.1244851. Epub Nov. 29, 2013.
Kurachi et al., The transcription factor BATF operates as an essential differentiation checkpoint in early effector CD8+ T cells. Nat Immunol. Apr. 2014;15(4):373-83. doi: 10.1038/ni.2834. Epub Mar. 2, 2014.
Kurtulus et al., TIGIT predominantly regulates the immune response via regulatory T cells. J Clin Invest. Nov. 2, 2015;125(11):4053-62. doi: 10.1172/JCI81187. Epub Sep. 28, 2015.
Lampe et al., Polyclonal B cell activation by the Eta-1 cytokine and the development of systemic autoimmune disease. J Immunol. Nov. 1, 1991;147(9):2902-6.
Lang et al., Asthma severity in childhood, untangling clinical phenotypes. Pediatr Allergy Immunol. Sep. 2010;21(6):945-53. doi: 10.1111/j.1399-3038.2010.01072.x.
Laurence et al., Interleukin-2 signaling via STAT5 constrains T helper 17 cell generation. Immunity. Mar. 2007;26(3):371-81.
Leavenworth et al., A p85α-osteopontin axis couples the receptor ICOS to sustained Bcl-6 expression by follicular helper and regulatory T cells. Nat Immunol. Jan. 2015;16(1):96-106. doi: 10.1038/ni.3050. Epub Dec. 1, 2014.
Leavenworth et al., Amelioration of arthritis through mobilization of peptide-specific CD8+ regulatory T cells. J Clin Invest. Mar. 1, 2013;123(3):1382-9. doi: 10.1172/JCI66938. Epub Feb. 8, 2013.
Leavenworth et al., Amelioration of arthritis through mobilization of peptide-specific CD8+ regulatory T cells. J Clin Invest. Mar. 2013;123(3):1382-9. doi: 10.1172/JCI66938. Epub Feb. 8, 2013.
Leavenworth et al., Analysis of the cellular mechanism underlying inhibition of EAE after treatment with anti-NKG2A F(ab')2. Proc Natl Acad Sci U S A. Feb. 9, 2010;107(6):2562-7. doi: 10.1073/pnas.0914732107. Epub Jan. 21, 2010.
Leavenworth et al., Mobilization of natural killer cells inhibits development of collagen-induced arthritis. Proc Natl Acad Sci U S A. Aug. 30, 2011;108(35):14584-9. doi: 10.1073/pnas.1112188108. Epub Aug. 22, 2011.
Lequin, Enzyme immunoassay (EIA)/enzyme-linked immunosorbent assay (ELISA). Clin Chem. Dec. 2005;51(12):2415-8. Epub Sep. 22, 2005.
Lim et al., Parkin mediates nonclassical, proteasomal-independent ubiquitination of synphilin-1: implications for Lewy body formation. J Neurosci. Feb. 23, 2005;25(8):2002-9.
Lindqvist et al., Prognostic laboratory markers of joint damage in rheumatoid arthritis. Ann Rheum Dis. Feb. 2005;64(2):196-201. Epub Sep. 30, 2004.
Linterman et al., Foxp3+ follicular regulatory T cells control T follicular helper cells and the germinal center reponse. Nat Med. Jul. 24, 2011;17(8):975-82. doi: 10.1038/nm.2425.
Lister et al., Report of a committee convened to discuss the evaluation and staging of patients with Hodgkin's disease: Cotswolds meeting. J Clin Oncol. Nov. 1989;7(11):1630-6. Erratum in: J Clin Oncol Sep. 1990;8(9):1602.
Liston et al., Homeostatic control of regulatory T cell diversity. Nat Rev Immunol. Mar. 2014;14(3):154-65. doi: 10.1038/nri3605. Epub Jan. 31, 2014.
Littman et al., Th17 and regulatory T cells in mediating and restraining inflammation. Cell. Mar. 19, 2010;140(6):845-58.
Lo et al., Molecular mimicry mediated by MHC class Ib molecules after infection with gram-negative pathogens. Nat Med. Feb. 2000;6(2):215-8.
Lo et al., T cell responses to Gram-negative intracellular bacterial pathogens: a role for CD8+ T cells in immunity to *Salmonella* infection and the involvement of MHC class Ib molecules. J Immunol. May 1, 1999;162(9):5398-406.
Lu et al., Induction of CD8+ regulatory T cells protects macaques against SIV challenge. Cell Rep. Dec. 27, 2012;2(6):1736-46. doi: 10.1016/j.celrep.2012.11.016. Epub Dec. 20, 2012.
Lu et al., Regulation of CD8+ regulatory T cells: Interruption of the NKG2A-Qa-1 interaction allows robust suppressive activity and resolution of autoimmune disease. Proc Natl Acad Sci U S A. Dec. 9, 2008;105(49):19420-5.
Lublin et al., Defining the clinical course of multiple sclerosis: results of an international survey. National Multiple Sclerosis Society (USA) Advisory Committee on Clinical Trials of New Agents in Multiple Sclerosis. Neurology. Apr. 1996;46(4):907-11.
Ma et al., Human T follicular helper (Tfh) cells and disease. Immunol Cell Biol. Jan. 2014;92(1):64-71. doi: 10.1038/icb.2013.55. Epub Oct. 22, 2013.
Ma et al., The origins, function, and regulation of T follicular helper cells. J Exp Med. Jul. 2, 2012;209(7):1241-53. doi:10.1084/jem.20120994.
Mahoney et al., Combination cancer immunotherapy and new immunomodulatory targets. Nat Rev Drug Discov. Aug. 2015;14(8):561-84. doi: 10.1038/nrd4591.
Malandro et al., Clonal Abundance of Tumor-Specific CD4(+) T Cells Potentiates Efficacy and Alters Susceptibility to Exhaustion. Immunity. Jan. 19, 2016;44(1):179-193. doi: 10.1016/j.immuni.2015.12.018.
Malchow et al., Aire-dependent thymic development of tumor-associated regulatory T cells. Science. Mar. 8, 2013;339(6124):1219-24. doi: 10.1126/science.1233913.
Martin et al., Defective CD95/APO-1/Fas signal complex formation in the human autoimmune lymphoproliferative syndrome, type Ia. Proc Natl Acad Sci U S A. Apr. 13, 1999;96(8):4552-7. Erratum in: Proc Natl Acad Sci U S A. May 18, 2004;101(20):7840.
Medeiros et al., Anaplastic Large Cell Lymphoma. Am J Clin Pathol. May 2007;127(5):707-22.
Mestas et al., Of mice and not men: differences between mouse and human immunology. J Immunol. Mar. 1, 2004;172(5):2731-8.
Miller et al., Clinically isolated syndromes suggestive of multiple sclerosis, part I: natural history, pathogenesis, diagnosis, and prognosis. Lancet Neurol. May 2005;4(5):281-8.

(56) References Cited

OTHER PUBLICATIONS

Mingari et al., Human CD8+ T lymphocyte subsets that express HLA class I-specific inhibitory receptors represent oligoclonally or monoclonally expanded cell populations. Proc Natl Acad Sci U S A. Oct. 29, 1996;93(22):12433-8.
Mingari et al., Regulation of KIR expression in human T cells: a safety mechanism that may impair protective T-cell responses. Immunol Today. Apr. 1998;19(4):153-7.
Mishima et al., High plasma osteopontin levels in patients with inflammatory bowel disease. J Clin Gastroenterol. Feb. 2007;41(2):167-72.
Miyao et al., Plasticity of Foxp3(+) T cells reflects promiscuous Foxp3 expression in conventional T cells but not reprogramming of regulatory T cells. Immunity. Feb. 24, 2012;36(2):262-75. doi: 10.1016/j.immuni.2011.12.012. Epub Feb. 9, 2012.
Modesti, Fluorescent labeling of proteins. Methods Mol Biol. 2011;783:101-20. doi: 10.1007/978-1-61779-282-3_6.
Mok et al., A prospective study of survival and prognostic indicators of systemic lupus erythematosus in a southern Chinese population. Rheumatology (Oxford). Apr. 2000;39(4):399-406.
Morel et al., Genetic reconstitution of systemic lupus erythematosus immunopathology with polycongenic murine strains. Proc Natl Acad Sci U S A. Jun. 6, 2000;97(12):6670-5.
Moretta et al., NK-CTLs, a novel HLA-E-restricted T-cell subset. Trends Immunol. Mar. 2003;24(3):136-43.
Moser et al., CD94-NKG2A receptors regulate antiviral CD8(+) T cell responses. Nat Immunol. Feb. 2002;3(2):189-95. Epub Jan. 22, 2002.
Mourmouras et al., Evaluation of tumour-infiltrating CD4+CD25+ FOXP3+ regulatory T cells in human cutaneous benign and atypical naevi, melanomas and melanoma metastases. Br J Dermatol. Sep. 2007;157(3):531-9. Epub Jun. 26, 2007.
Mrowietz et al., Definition of treatment goals for moderate to severe psoriasis: a European consensus. Arch Dermatol Res. Jan. 2011;303(1):2-10. doi: 10.1007/s00403-010-1080-1. Epub Sep. 21, 2010.
Münst et al., Engineering cell-permeable protein. J Vis Exp. Dec. 28, 2009;(34). pii: 1627. doi: 10.3791/1627.
Murphy et al., Anaphylaxis caused by repetitive doses of a GITR agonist monoclonal antibody in mice. Blood. Apr. 3, 2014;123(14):2172-80. doi: 10.1182/blood-2013-12-544742. Epub Feb. 20, 2014.
Nahar, Covalent immobilization of proteins onto photoactivated polystyrene microtiter plates for enzyme-linked immunosorbent assay procedures. Protocol Exchange Dec. 5, 2013.
Nakagawa et al., Instability of Helios-deficient Tregs is associated with conversion to a T-effector phenotype and enhanced antitumor immunity. Proc Natl Acad Sci U S A. May 31, 2016;113(22):6248-53. doi: 10.1073/pnas.1604765113. Epub May 16, 2016.
Nakase et al., Overexpression of novel short isoforms of Helios in a patient with T-cell acute lymphoblastic leukemia. Exp Hematol. Apr. 2002;30(4):313-7.
Nakayamada et al.,Type I IFN induces binding of STAT1 to Bcl6: divergent roles of STAT family transcription factors in the T follicular helper cell genetic program. J Immunol. Mar. 1, 2014;192(5):2156-66. doi: 10.4049/jimmunol.1300675. Epub Jan. 31, 2014.
Ngiow et al., Anti-TIM3 antibody promotes T cell IFN-γ-mediated antitumor immunity and suppresses established tumors. Cancer Res. May 15, 2011;71(10):3540-51. doi: 10.1158/0008-5472.CAN-11-0096. Epub Mar. 23, 2011.
Nishikawa et al., Regulatory T cells in cancer immunotherapy. Curr Opin Immunol. Apr. 2014;27:1-7. doi: 10.1016/j.coi.2013.12.005. Epub Jan. 14, 2014.
Nurieva et al., Bcl6 mediates the development of T follicular helper cells. Science. Aug. 21, 2009;325(5943):1001-5. doi: 10.1126/science.1176676. Epub Jul. 23, 2009.
Obenauer et al., Scansite 2.0: Proteome-wide prediction of cell signaling interactions using short sequence motifs. Nucleic Acids Res. Jul. 1, 2003;31(13):3635-41.
O'Herrin et al., Antigen-specific blockade of T cells in vivo using dimeric MHC peptide. J Immunol. Sep. 1, 2001;167(5):2555-60.
Ohinata et al.,Blimp1 is a critical determinant of the germ cell lineage in mice. Nature. Jul. 14, 2005;436(7048):207-13. Epub Jun. 5, 2005.
Ohkura et al., T cell receptor stimulation-induced epigenetic changes and Foxp3 expression are independent and complementary events required for Treg cell development. Immunity. Nov. 16, 2012;37(5):785-99. doi:10.1016/j.immuni.2012.09.010. Epub Nov. 1, 2012.
O'Shea et al., Genomic views of STAT function in CD4+ T helper cell differentiation. Nat Rev Immunol. Apr. 2011;11(4):239-50. doi: 10.1038/nri2958.
Page et al., Immune modulation in cancer with antibodies. Annu Rev Med. 2014;65:185-202. doi: 10.1146/annurev-med-092012-112807. Epub Oct. 30, 2013.
Panoutsakopoulou et al., Analysis of the relationship between viral infection and autoimmune disease. Immunity. Jul. 2001;15(1):137-47.
Pardoll, The blockade of immune checkpoints in cancer immunotherapy. Nat Rev Cancer. Mar. 22, 2012;12(4):252-64. doi: 10.1038/nrc3239.
Park et al., Modulation of CD4+ T lymphocyte lineage outcomes with targeted, nanoparticle-mediated cytokine delivery. Mol Pharm. Feb. 7, 2011;8(1):143-52. doi: 10.1021/mp100203a. Epub Dec. 8, 2010.
Park et al., The regulatory subunits of PI3K, p85alpha and p85beta, interact with XBP-1 and increase its nuclear translocation. Nat Med. Apr. 2010;16(4):429-37. doi: 10.1038/nm.2099. Epub Mar. 28, 2010.
Patarca et al., Differential induction of interferon gamma gene expression after activation of CD4+ T cells by conventional antigen and Mls superantigen. Proc Natl Acad Sci U S A. Apr. 1, 1991;88(7):2736-9.
Patarca et al., Dysregulated expression of the T cell cytokine Eta-1 in CD4-8-lymphocytes during the development of murine autoimmune disease. J Exp Med. Oct. 1, 1990;172(4):1177-83.
Pedersen et al., Development of assay platforms for in vitro screening of Treg modulating potential of pharmacological compounds. Immunopharmacol Immunotoxicol. Feb. 2015;37(1):63-71. doi: 10.3109/08923973.2014.977449. Epub Nov. 4, 2014.
Petrovas et al., SIV-specific CD8+ T cells express high levels of PD1 and cytokines but have impaired proliferative capacity in acute and chronic SIVmac251 infection. Blood. Aug. 1, 2007;110(3):928-36. Epub Apr. 17, 2007.
Pierson et al., Antiapoptotic Mcl-1 is critical for the survival and niche-filling capacity of Foxp3+ regulatory T cells. Nat Immunol. Sep. 2013;14(9):959-65. doi:10.1038/ni.2649. Epub Jul. 14, 2013.
Pietra et al., The analysis of the natural killer-like activity of human cytolytic T lymphocytes revealed HLA-E as a novel target for TCR alpha/beta-mediated recognition. Eur J Immunol. Dec. 2001;31(12):3687-93.
Pisitkun et al., Autoreactive B cell responses to RNA-related antigens due to TLR7 gene duplication. Science. Jun. 16, 2006;312(5780):1669-72. Epub May 18, 2006.
Platt et al., CRISPR-Cas9 knockin mice for genome editing and cancer modeling. Cell. Oct. 9, 2014;159(2):440-55. doi: 10.1016/j.cell.2014.09.014. Epub Sep. 25, 2014.
Polo et al., Specific peptide interference reveals BCL6 transcriptional and oncogenic mechanisms in B-cell lymphoma cells. Nat Med. Dec. 2004;10(12):1329-35. Epub Nov. 7, 2004.
Powell et al., Expression profiling of a hemopoietic cell survival transcriptome implicates osteopontin as a functional prognostic factor in AML. Blood. Nov. 26, 2009;114(23):4859-70. doi:10.1182/blood-2009-02-204818. Epub Oct. 5, 2009.
Quezada et al., Tumor-reactive CD4(+) T cells develop cytotoxic activity and eradicate large established melanoma after transfer into lymphopenic hosts. J Exp Med. Mar. 15, 2010;207(3):637-50. doi: 10.1084/jem.20091918. Epub Feb. 15, 2010.
Roger et al., Cutting edge: Ly49A inhibits TCR/CD3-induced apoptosis and IL-2 secretion. J Immunol. Jul. 1, 2001;167(1):6-10.
Roifman et al., Evidence of endothelial dysfunction in patients with inflammatory bowel disease. Clin Gastroenterol Hepatol. Feb. 2009;7(2):175-82. doi: 10.1016/j.cgh.2008.10.021. Epub Oct. 30, 2008.

(56) References Cited

OTHER PUBLICATIONS

Rojas et al., Genetic engineering of proteins with cell membrane permeability. Nat Biotechnol. Apr. 1998;16(4):370-5.
Rolf et al., Phosphoinositide 3-kinase activity in T cells regulates the magnitude of the germinal center reaction. J Immunol. Oct. 1, 2010;185(7):4042-52. doi: 10.4049/jimmunol.1001730. Epub Sep. 8, 2010.
Rolf et al., Signaling pathways in T follicular helper cells. J Immunol. Jun. 15, 2010;184(12):6563-8. doi: 10.4049/jimmunol.1000202.
Roy et al., Blimp-1 specifies neural crest and sensory neuron progenitors in the zebrafish embryo. Curr Biol. Oct. 5, 2004;14(19):1772-7.
Rubtsov et al., Stability of the regulatory T cell lineage in vivo. Science. Sep. 24, 2010;329(5999):1667-71. doi: 10.1126/science.1191996.
Rullo et al., Plasma levels of osteopontin identify patients at risk for organ damage in systemic lupus erythematosus. Arthritis Res Ther. Jan. 23, 2013;15(1):R18. doi: 10.1186/ar4150.
Rutishauser et al.,Transcriptional repressor Blimp-1 promotes CD8(+) T cell terminal differentiation and represses the acquisition of central memory T cell properties. Immunity. Aug. 21, 2009;31(2):296-308. doi:10.1016/j.immuni.2009.05.014. Epub Aug. 6, 2009.
Sage et al., PD-1 controls Lymph Node and Blood T Follicular Regulatory Cells. Nat Immunol. Feb. 2013;14(2):152-61. doi: 10.1038/ni.2496. Epub Dec. 16, 2012.
Sakaguchi et al., Regulatory T cells and immune tolerance. Cell. May 30, 2008;133(5):775-87.
Sakuishi et al., Targeting Tim-3 and PD-1 pathways to reverse T cell exhaustion and restore anti-tumor immunity. J Exp Med. Sep. 27, 2010;207(10):2187-94. doi:10.1084/jem.20100643. Epub Sep. 6, 2010. Erratum in: J Exp Med. Jun. 6, 2011;208(6):1331.
Sakuishi et al., TIM3+FOXP3+ regulatory T cells are tissue-specific promoters of T-cell dysfunction in cancer. Oncoimmunology. Apr. 1, 2013;2(4):e23849.
Samitas et al., Osteopontin expression and relation to disease severity in human asthma. Eur Respir J. Feb. 2011;37(2):331-41. doi: 10.1183/09031936.00017810. Epub Jun. 18, 2010.
Sasaki et al., Function of PI3Kgamma in thymocyte development, T cell activation, and neutrophil migration. Science. Feb. 11, 2000;287(5455):1040-6.
Sato et al., Osteopontin/Eta-1 upregulated in Crohn's disease regulates theTh1 immune response. Gut. Sep. 2005;54(9):1254-62.
Scanlan et al., Cancer/testis antigens: an expanding family of targets for cancer immunotherapy. Immunol Rev. Oct. 2002;188:22-32.
Schaer et al., GITR pathway activation abrogates tumor immune suppression through loss of regulatory T cell lineage stability. Cancer Immunol Res. Nov. 2013;1(5):320-31. doi: 10.1158/2326-6066.CIR-13-0086.
Schafer et al., Microglia sculpt postnatal neural circuits in an activity and complement-dependent manner. Neuron. May 24, 2012;74(4):691-705. doi: 10.1016/j.neuron.2012.03.026.
Scott et al., Antibody therapy of cancer. Nat Rev Cancer. Mar. 22, 2012;12(4):278-87. doi: 10.1038/nrc3236.
Sebastian et al., Helios Controls a Limited Subset of Regulatory T Cell Functions. J Immunol. Jan. 1, 2016;196(1):144-55. doi: 10.4049/jimmunol.1501704. Epub Nov. 18, 2015.
Shimizu et al., Stimulation of CD25(+)CD4(+) regulatory T cells through GITR breaks immunological self-tolerance. Nat Immunol. Feb. 2002;3(2):135-42. Epub Jan. 22, 2002.
Shin et al., A role for the transcriptional repressor Blimp-1 in CD8(+) T cell exhaustion during chronic viral infection. Immunity. Aug. 21, 2009;31(2):309-20. doi:10.1016/j.immuni.2009.06.019. Epub Aug. 6, 2009.
Shinohara et al., Alternative translation of osteopontin generates intracellular and secreted isoforms that mediate distinct biological activities in dendritic cells. Proc Natl Acad Sci U S A. May 20, 2008;105(20):7235-9. doi: 10.1073/pnas.0802301105. Epub May 14, 2008.

Shinohara et al., Engagement of the type I interferon receptor on dendritic cells inhibits T helper 17 cell development: role of intracellular osteopontin. Immunity. Jul. 18, 2008;29(1):68-78. doi:10.1016/j.immuni.2008.05.008.
Shinohara et al., T-bet-dependent expression of osteopontin contributes to T cell polarization. Proc Natl Acad Sci U S A. Nov. 22, 2005;102(47):17101-6. Epub Nov. 14, 2005.
Simpson et al., Fc-dependent depletion of tumor-infiltrating regulatory T cells co-deftnes the efficacy of anti-CTLA-4 therapy against melanoma. J Exp Med. Aug. 26, 2013;210(9):1695-710. doi: 10.1084/jem.20130579. Epub Jul. 29, 2013.
Slifka et al., Preferential escape of subdominant CD8+ T cells during negative selection results in an altered antiviral T cell hierarchy. J Immunol. Feb. 1, 2003;170(3):1231-9.
Soloski et al., Structural and functional characteristics of the class IB molecule, Qa-1. Immunol Rev. Oct. 1995;147:67-89.
Speiser et al., In vivo expression of natural killer cell inhibitory receptors by human melanoma-specific cytolytic T lymphocytes. J Exp Med. Sep. 20, 1999;190(6):775-82.
Subramanian et al., A Tlr7 translocation accelerates systemic autoimmunity in murine lupus. Proc Natl Acad Sci U S A. Jun. 27, 2006;103(26):9970-5. Epub Jun. 15, 2006.
Sugimoto et al., Foxp3-dependent and -independent molecules specific for CD25+CD4+ natural regulatory T cells revealed by DNA microarray analysis. Int Immunol. Aug. 2006;18(8):1197-209. Epub Jun. 13, 2006.
Sugiyama et al., Anti-CCR4 mAb selectively depletes effector-type FoxP3+CD4+ regulatory T cells, evoking antitumor immune responses in humans. Proc Natl Acad Sci U S A. Oct. 29, 2013;110(44):17945-50. doi: 10.1073/pnas.1316796110. Epub Oct. 14, 2013.
Sullivan et al., Positive selection of a Qa-1-restricted T cell receptor with specificity for insulin. Immunity. Jul. 2002;17(1):95-105.
Tafuri et al., ICOS is essential for effective T-helper-cell responses. Nature. Jan. 4, 2001;409(6816):105-9.
Takahashi et al., Role of ERas in promoting tumour-like properties in mouse embryonic stem cells. Nature. May 29, 2003;423(6939):541-5.
Tarner et al., Treatment of autoimmune disease by adoptive cellular gene therapy. Ann N Y Acad Sci. Sep. 2003;998:512-9.
Tey et al., Adoptive T-cell transfer in cancer immunotherapy. Immunol Cell Biol. Jun. 2006;84(3):281-9.
Thompson et al., Prognosis and prognostic factors in inflammatory bowel disease. Saudi J Gastroenterol. Sep. 1995;1(3):129-37.
Thornton et al., Expression of Helios, an Ikaros transcription factor family member, differentiates thymic-derived from peripherally induced Foxp3+ T regulatory cells. J Immunol. Apr. 1, 2010;184(7):3433-41.
Tompkins et al., Transporters associated with antigen processing (TAP)-independent presentation of soluble insulin to alpha/beta T cells by the class Ib gene product, Qa-1(b). J Exp Med. Sep. 7, 1998;188(5):961-71.
Transy et al., A low polymorphic mouse H-2 class I gene from the Tla complex is expressed in a broad variety of cell types. J Exp Med. Aug. 1, 1987;166(2):341-61.
Tsang et al., Multiple sclerosis—diagnosis, management and prognosis. Aust Fam Physician. Dec. 2011;40(12):948-55.
Tun et al., Pathway analysis of primary central nervous system lymphoma. Blood. Mar. 15, 2008;111(6):3200-10. doi: 10.1182/blood-2007-10-119099. Epub Jan. 9, 2008.
Uede et al., Osteopontin, intrinsic tissue regulator of intractable inflammatory diseases. Pathol. Int. 2011;61:265-280.
Ugolini et al., Involvement of inhibitory NKRs in the survival of a subset of memory-phenotype CD8+ T cells. Nat Immunol. May 2001;2(5):430-5. Erratum in: Nat Immunol Jul. 2001;2(7):658.
UNIPROT Submission; Accession No. P40933: Grabstein et al; Feb. 1, 1995; 2 pages.
Van Den Berg et al., Protein transduction domain delivery of therapeutic macromolecules. Curr Opin Biotechnol. Dec. 2011;22(6):888-93. doi:10.1016/j.copbio.2011.03.008. Epub Apr. 12, 2011.

(56) References Cited

OTHER PUBLICATIONS

Viguier et al., Foxp3 expressing CD4+CD25(high) regulatory T cells are overrepresented in human metastatic melanoma lymph nodes and inhibit the function of infiltrating T cells. J Immunol. Jul. 15, 2004;173(2):1444-53.
Vinuesa et al., A RING-type ubiquitin ligase family member required to repress follicular helper T cells and autoimmunity. Nature. May 26, 2005;435(7041):452-8.
Vivier et al., Inhibitory NK-cell receptors on T cells: witness of the past, actors of the future. Nat Rev Immunol. Mar. 2004;4(3):190-8.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wan et al., Regulatory T-cell functions are subverted and converted owing to attenuated Foxp3 expression. Nature. Feb. 15, 2007;445(7129):766-70. Epub Jan. 14, 2007.
Wang et al., CD8 regulatory T cells: what's old is now new. Immunol Cell Biol. Mar.-Apr. 2009;87(3):192-3. doi: 10.1038/icb.2009.8. Epub Feb. 24, 2009.
Weinmayr et al., Asthma phenotypes identified by latent class analysis in the ISAAC phase II Spain study. Clin Exp Allergy. Feb. 2013;43(2):223-32. doi: 10.1111/cea.12035.
Wherry, T cell exhaustion. Nat Immunol. Jun. 2011;12(6):492-9.
Wieczorek et al., Genetically modified T cells for the treatment of malignant disease. Transfus Med Hemother. Dec. 2013;40(6):388-402. doi:10.1159/000357163. Epub Nov. 29, 2013.
Winnay et al., A Novel Interaction Between the Regulatory Subunit of PI 3-Kinase and X-box Binding Portein-1 Modulates the Unfolded Protein Response. Nat Med. Apr. 2010;16(4):438-45. doi: 10.1038/nm.2121. Epub Mar. 28, 2010.
Wong et al., Elevation of plasma osteopontin concentration is correlated with disease activity in patients with systemic lupus erythematosus. Rheumatology (Oxford). May 2005;44(5):602-6. Epub Feb. 10, 2005.
Xiao et al., GITR subverts Foxp3+ Tregs to boost Th9 immunity through regulation of histone acetylation. Nature Communications. Sep. 14, 2015;6:8266.
Xu et al., Follicular T-helper cell recruitment governed by bystander B cells and ICOS-driven motility. Nature. Apr. 25, 2013;496(7446):523-7. doi:10.1038/nature12058.
Yaffe et al., A motif-based profile scanning approach for genome-wide prediction of signaling pathways. Nat Biotechnol. Apr. 2001;19(4):348-53.
Yaffe et al., The structural basis for 14-3-3:phosphopeptide binding specificity. Cell. Dec. 26, 1997;91(7):961-71.
Yamaguchi et al., Control of immune responses by antigen-specific regulatory T cells expressing the folate receptor. Immunity. Jul. 2007;27(1):145-59. Epub Jul. 5, 2007.
Yang et al., Opposing regulation of the locus encoding IL-17 through direct, reciprocal actions of STAT3 and STAT5. Nat Immunol. Mar. 2011;12(3):247-54. doi: 10.1038/ni.1995. Epub Jan. 30, 2011.
Yao et al., Nonredundant roles for Stat5a/b in directly regulating Foxp3. Blood. May 15, 2007;109(10):4368-75. Epub Jan. 16, 2007.
Yawn, Factors accounting for asthma variability: achieving optimal symptom control for individual patients. Prim Care Respir J. Sep. 2008;17(3):138-47. doi: 10.3132/pcrj.2008.00004.
Yin et al., Ezh2 regulates differentiation and function of natural killer cells through histone methyltransferase activity. Proc Natl Acad Sci U S A. Dec. 29, 2015;112(52):15988-93. doi: 10.1073/pnas.1521740112. Epub Dec. 14, 2015.
Young et al., Differential expression of leukocyte receptor complex-encoded Ig-like receptors correlates with the transition from effector to memory CTL. J Immunol. Mar. 15, 2001;166(6):3933-41.
Yu et al., Roquin represses autoimmunity by limiting inducible T-cell co-stimulator messenger RNA. Nature. Nov. 8, 2007;450(7167):299-303. doi: 10.1038/nature06253. Erratum in: Nature. Feb. 21, 2008;451(7181):1022.
Yu et al., The transcriptional repressor Bcl-6 directs T follicular helper cell lineage commitment. Immunity. Sep. 18, 2009;31(3):457-68. doi:10.1016/j.immuni.2009.07.002. Epub Jul. 23, 2009.
Yu et al.., Regulation of the p85/p110 phosphatidylinositol 3'-kinase: stabilization and inhibition of the p110alpha catalytic subunit by the p85 regulatory subunit. Mol Cell Biol. Mar. 1998;18(3):1379-87.
Zeng et al., Synergy of IL-21 and IL-15 in regulating CD8+ T cell expansion and function. J Exp Med. Jan. 3, 2005;201(1):139-48.
Zeug et al., Quantitative intensity-based FRET approaches—a comparative snapshot. Biophys J. Nov. 7, 2012;103(9):1821-7.doi:10.1016/j.bpj.2012.09.031.
Zhang et al., Potent and selective stimulation of memory-phenotype CD8+ T cells in vivo by IL 15. Immunity. May 1998;8(5):591-9.
Zhao et al., The oncogenic properties of mutant p110alpha and p110beta phosphatidylinositol 3-kinases in human mammary epithelial cells. Proc Natl Acad Sci U S A. Dec. 20, 2005;102(51):18443-8. Epub Dec. 8, 2005.
Zhu et al., The Tim-3 ligand galectin-9 negatively regulates T helper type 1 immunity. Nat Immunol. Dec. 2005;6(12):1245-52. Epub Nov. 13, 2005.
Zorn et al., IL-2 regulates FOXP3 expression in human CD4+CD25+ regulatory T cells through a STAT-dependent mechanism and induces the expansion of these cells in vivo. Blood. Sep. 1, 2006;108(5):1571-9. Epub Apr. 27, 2006.
Zou, Regulatory T cells, tumour immunity and immunotherapy. Nat Rev Immunol. Apr. 2006;6(4):295-307.

\* cited by examiner

NCBI Reference Sequence: NP_000576.1 (Human Il-15): SEQ ID NO: 3 mriskphlrs isiqcylcll lnshflteag ihvfilgcfs aglpkteanw vnvisdlkki
edliqsmhid atlytesdvh psckvtamkc fllelqvisl esgdasihdt venliilann
slssngnvte sgckeceele eknikeflqs fvhivqmfin ts

TARGETED EXPANSION OF QA-1-PEPTIDE-SPECIFIC REGULATORY CD8 T CELLS TO AMELIORATE ARTHRITIS

RELATED APPLICATIONS

This application is a continuation of U.S. Non-Provisional application Ser. No. 14/431,113, filed Mar. 25, 2015, which is a national stage of International Application No. PCT/US2013/061851, filed Sep. 26, 2013, which was published under PCT Article 21(2) in English and which claims the benefit under 35 U.S.C. § 119(e) of U.S. Provisional Application Nos. 61/707,357, filed Sep. 28, 2012, and 61/773,959, filed Mar. 7, 2013, the entire contents of which are hereby incorporated by reference.

FEDERALLY SPONSORED RESEARCH

This invention was made with Government support under Grant Nos. CA070083 and AI037562 awarded by the National Institutes of Health. The Government has certain rights in this invention.

FIELD OF THE INVENTION

The present invention relates to nanoparticles and methods for treating autoimmune diseases.

BACKGROUND OF THE INVENTION

Achieving a balance between induction of protective immunity against pathogens and maintenance of self-tolerance is a central feature of the adaptive immune system. Although negative selection in the thymus removes the majority of clones that express T cell receptors (TCR) with high affinity for self-peptide MHC products, this process is incomplete. A significant fraction of mature peripheral T cells that respond to self-peptide-MHC complexes may differentiate into effector cells in the context of inflammatory stimuli (Bouneaud et al., 2000; Goldrath and Bevan, 1999; Slifka et al., 2003). Although this process is constrained by abortive or defective TCR signaling resulting in cellular elimination (AICD) or inactivation (Martin et al., 1999; Kearney et al., 1994), these cell-intrinsic mechanisms may not suffice to prevent the development of autoimmune disorders (Anderton et al., 2001; Panoutsakopoulou et al., 2001). There is increasing evidence that self-tolerance may also depend on inhibitory interactions between effector T cells and regulatory or suppressive cells (Littman and Rudensky, 2010). A regulatory subset of CD8+ T cells, termed CD8+ Treg cells, has been found to inhibit follicular T helper cell responses, which are essential for production of autoantibodies and formation of ectopic germinal centers (GC). However, the potential contribution of CD8+ Treg cells to the pathogenesis and treatment of autoimmune disease is not well understood. Due to the severity and breath of autoimmune diseases such as lupus and rheumatoid arthritis, there is a great need for effective treatments of such diseases.

SUMMARY OF THE INVENTION

The present invention, in one aspect, relates to the development of strategies based on in vivo and in vitro expansion and activation of the CD8+ Treg cells for the treatment of autoimmune diseases.

In some aspects provided, is a composition for a nanoparticle comprising a biocompatible polymer and a complex, wherein the complex is a major histocompatibility complex (MHC) class 1 antigen E (HLA-E) linked to a peptide, and wherein the HLA-E-peptide complex is linked to the surface of the nanoparticle. In certain embodiments, at least 4 units, at least 5, at least 6, at least 7, at least 8, at least 9 or at least 10 units of the HLA-E-peptide complex are linked together to form a moiety and the moiety is linked to the surface of the nanoparticle. In certain embodiments of the invention, the HLA-E-peptide complex of this nanoparticle composition comprises biotin, and the complexes are linked together through biotin-avidin interaction to form the moiety. In certain embodiments of the invention, the peptide linked to the HLA-E is selected from the group consisting of $Hsp60_{p216}$, B7sp and FL9. In certain embodiments, the HLA-E-peptide complex or the moiety is linked to the surface of the nanoparticle via PEGylation.

In certain embodiments, the peptide of this complex is linked to HLA-E via a flexible linker. In certain embodiments, wherein the peptide is linked to HLA-E via a flexible linker, this linker is a Gly-Ser linker.

In certain embodiments, the heavy chain and light chain ($\beta$-2 microglobulin) of the HLA-E are linked via a flexible linker. In certain embodiments, wherein the heavy chain and light chain ($\beta$-2 microglobulin) of the HLA-E are linked via a flexible linker, the flexible linker is a Gly-Ser linker.

In certain embodiments, the biocompatible polymer of the nanoparticle is selected from the group consisting of poly(lactic-co-glycolic acid) (PLGA), poly(ethylene glycol) (PEG), chitosan, and chitosan-PEG. In certain embodiments of the nanoparticle composition, a low releasing dose of IL-15 is incorporated into the nanoparticle.

In other aspects provided, is a method for treating an autoimmune disease comprising: administering to a subject in need of such treatment nanoparticles, as described in the embodiments above, in an amount effective to ameliorate a symptom of the autoimmune disease. In certain embodiments of the invention, the autoimmune disease treated by the administration of nanoparticles is selected from a group consisting of systemic lupus erythematosus, chronic graft versus host disease, rheumatoid arthritis, insulin-dependent diabetes mellitus, multiple sclerosis, psoriasis, inflammatory bowel disease, Sjogren's syndrome, Graves disease, Crohn's disease. Waldenstrom's macroglobulinemia, hyperviscosity syndrome, monoclonal gammopathy of undetermined origin, POEMS syndrome, myeloma, macroglobulinemia, and cold agglutinin disease.

In other aspects provided, is a method for treating an autoimmune disease comprising: contacting dendritic cells isolated from a subject in need of such treatment with $Hsp60_{p216}$ peptide to generate $Hsp60_{p216}$-loaded dendritic cells; and administering to the subject the $Hsp60_{p216}$-loaded dendritic cells in an amount effective to ameliorate a symptom of the autoimmune disease. In certain embodiments the dendritic cells isolated from a subject in need of such treatment are contacted with $Hsp60_{p216}$ for 2, 4, 6, 8, 12, 16, 18 or 24 hours to generate $Hsp60_{p216}$-loaded dendritic cells. In certain embodiments of the invention, this method is used to treat autoimmune diseases selected from the group consisting of systemic lupus erythematosus, chronic graft versus host disease, rheumatoid arthritis, insulin-dependent diabetes mellitus, multiple sclerosis, psoriasis, inflammatory bowel disease, Sjogren's syndrome. Graves disease. Crohn's disease, Waldenstrom's macroglobulinemia, hyperviscosity syndrome, monoclonal gammopathy of undetermined origin, POEMS syndrome, myeloma, macroglobulinemia, and cold agglutinin disease.

In other aspects provided, is method for treating an autoimmune disease comprising: isolating from a subject in need of such treatment CD8+ T cells that bind $Hsp60_{p216}$ peptide; growing the isolated cells in a culture medium containing IL-15C until the number of CD8+ T cells that bind $Hsp60_{p216}$ peptide increases to at least 3-5% of CD8+ T cells, thereby producing a population of cells enriched with CD8+ T cells that bind $Hsp60_{p216}$ peptide; and administering CD8+ T cells that bind $Hsp60_{p216}$ peptide from the described population of cells to the subject in an amount effective to ameliorate a symptom of the autoimmune disease. In certain embodiments, the step of isolating CD8+ T cells that bind $Hsp60_{p216}$ peptide comprises sorting a sample containing T cells obtained from the subject into CD8+ T cells that bind $Hsp60_{p216}$ peptide using a fluorescently labeled moiety having at least 4 units of a complex, wherein the complex is a major histocompatibility complex (MHC) class I antigen E (HLA-E) linked to $Hsp60_{p216}$ peptide. In certain embodiments, the HLA-E-peptide complex described comprises biotin, and at least 4 such complexes associate through biotin-avidin interaction to form the moiety. In certain embodiments, avidin is fluorescently labeled. In certain embodiments, the fluorescent label used to label avidin is Phycoerythrin (PE). In certain embodiments, the population of cells enriched with CD8+ T cells that bind $Hsp60_{p216}$ peptide is further enriched using anti-R-Phycoerythrin (PE) microbeads. In certain embodiments, the autoimmune disease treated through these steps is selected from the group consisting of systemic lupus erythematosus, chronic graft versus host disease, rheumatoid arthritis, insulin-dependent diabetes mellitus, multiple sclerosis, psoriasis, inflammatory bowel disease, Sjogren's syndrome, Graves disease, Crohn's disease, Waldenstrom's macroglobulinemia, hyperviscosity syndrome, monoclonal gammopathy of undetermined origin, POEMS syndrome, myeloma, macroglobulinemia, and cold agglutinin disease.

In some aspects provided, is a method for treating HIV infection. The method comprises administering to a subject in need of such treatment nanoparticles described herein in an amount effective to ameliorate a symptom of the HIV infection.

In some aspects provided, is a method for treating HIV infection. The method comprises contacting dendritic cells isolated from a subject in need of such treatment with $Hsp60_{p216}$ peptide to generate $Hsp60_{p216}$-loaded dendritic cells; and administering to the subject the $Hsp60_{p216}$-loaded dendritic cells in an amount effective to ameliorate a symptom of the HIV infection. In certain embodiments, the dendritic cells are contacted with $Hsp60_{216}$ for 2, 4, 6, 8, 12, 16, 18 or 24 hours to generate $Hsp60_{p26}$-loaded dendritic cells.

In some aspects provided, is a method for treating HIV infection comprising: isolating from a subject in need of such treatment CD8+ T cells that bind $Hsp60_{p216}$ peptide; growing the isolated cells in a culture medium containing IL-15C until the number of CD8+ T cells that bind $Hsp60_{p216}$ peptide increases to at least 3-5% of CD8+T cells, thereby producing a population of cells enriched with CD8+ T cells that bind $Hsp60_{p216}$ peptide; and administering CD8+ T cells that bind $Hsp60_{p216}$ peptide from the population of cells to the subject in an amount effective to ameliorate a symptom of the HIV infection. In certain embodiments, the step of isolating CD8+ T cells that bind $Hsp60_{p216}$ peptide comprises sorting a sample containing T cells obtained from the subject into CD8+ T cells that bind $Hsp60_{p216}$ peptide using a fluorescently labeled moiety having at least 4 units of a complex, wherein the complex is a major histocompatibility complex (MHC) class I antigen E (HLA-E) linked to $Hsp60_{p216}$ peptide. In certain embodiments, the HLA-E-peptide complex described comprises biotin, and at least 4 such complexes associate through biotin-avidin interaction to form the moiety. In certain embodiments, avidin is fluorescently labeled. In certain embodiments, the fluorescent label used to label avidin is Phycoerythrin (PE). In certain embodiments, the population of cells enriched with CD8+ T cells that bind $Hsp60_{p216}$ peptide is further enriched using anti-R-Phycoerythrin (PE) microbeads.

Each of the embodiments and aspects of the invention can be practiced independently or combined. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description. Each aspect of the invention can encompass various embodiments as will be understood.

All documents identified in this application are incorporated in their entirety herein by reference.

DETAILED DESCRIPTION OF THE INVENTION

Figure 1A:
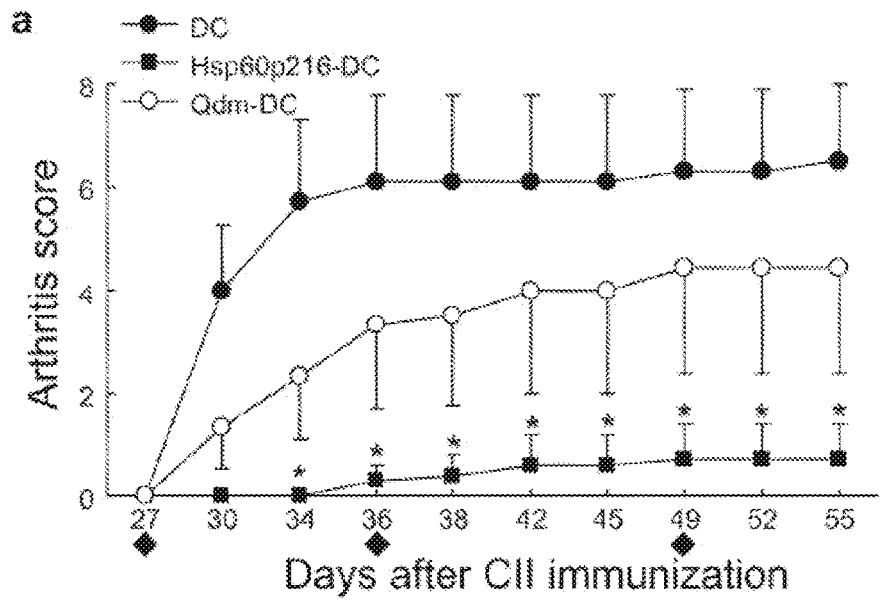
FIG. 1A is graph showing that selective expansion of Qa-1-restricted CD8+ Treg inhibits arthritis. Arthritis was induced in C57BL/6 mice as described in Methods. Irradiated LPS-activated $Kb^{-/-}Db^{-/-}$ bone marrow-derived DC pre-loaded with or without indicated peptides was injected subcutaneously at the tail base at d27, d36 and d49 ( ). Arthritis scores are shown; 5-6 mice per group. Group (DC alone) versus group (Hsp60p216-DC), *P<0.05.

A subpopulation of CD8+ regulatory T cells is essential for maintenance of self-tolerance and prevention of autoimmune disease (WO 2012/054509 incorporated by reference herein). These CD8+ Treg cells are programmed to suppress rather than activate immunity and represent an essential regulatory element of the immune response and a guarantor of self-tolerance. The present invention, in one aspect, relates to the development of strategies based on in vivo and in vitro expansion and activation of the CD8+ Treg cells for the treatment of autoimmune diseases.

The specialized regulatory CD8+ T cells selectively suppress CD4+ follicular helper T cell (TFH) activity through perforin-dependent lysis by recognition of class Ib major histocompatibility complex (MHC) peptide Qa-1 (mouse homolog of human leukocyte antigen E (HLA-E)) expressed at the surface of TFH cells and dampen autoantibody responses. Qa-1, the mouse homolog of human leukocyte antigen E (HLA-E), forms a heterodimer with $\beta_2$-microglobulin that binds to and presents peptides derived from self or foreign proteins after deliberate immunization or infection (Lo et al., 1999; Lo et al., 2000; Sullivan et al., 2002).

Three peptides are presented by Qa-1 (HLA-E): Qdm (B7sp in humans), Hsp60$_{p216}$ and FL9. Qa-1 heterodimers containing peptides derived from MHC class Ia leader sequences, called Qdm (for Qa-1 determinant modifier), bind to nonclonally distributed CD94-NKG2A receptors expressed by natural killer (NK) cells and a subpopulation of CD8+ T cells. The functional consequence of Qa-1/Qdm-NKG2A interactions is generally inhibition of NK or CD8 cytolytic activity (Moser et al., 2002). Hsp60$_{p216}$ peptide (GMKFDRGYI; SEQ ID NO: 1) contains residues 216-224 of the 60 kD heat shock protein (Hsp). The Hsp60$_{p216}$ peptide can efficiently replace Qdm peptides under conditions of cellular activation and stress. A third peptide that is presented by Qa-1 under conditions of defective antigen processing in the endoplasmic reticulum (ERAAP dysfunction) is the highly conserved peptide FL9, FYAEATPML (SEQ ID NO: 2), which is derived from the conservative Fam49b gene. Recognition of Qa-1/FL9 by CD8 T cells may serve to eliminate abnormal cells that have defects in antigen presentation.

One of the potential platforms for specific expansion of Qa-1-restricted or HLA-E-restricted CD8+ Treg is based on vaccination or treatment with peptide-Qa-1 (HLA-E)-coated nanoparticles (p-Qa-1(HLA-E)-NP). Administration of nanoparticles conjugated with Qa-1 tetramers without co-stimulatory activity is competent to stimulate Qa-1-peptide-specific CD8 T cells, since CD8+ Treg are memory cells according to function and phenotype. Unlike naïve CD8 cells, memory cells can be stimulated to expand by antigen presented without co-stimulation.

Accordingly, aspects of the invention involve nanoparticles (NP) comprising a biocompatible polymer and a complex of MHC class I antigen E (HLA-E) linked to a peptide. The HLA-E-peptide complex is linked to the surface of the nanoparticle to ensure efficient exposure to TCR on CD8 cells. To enhance the efficiency of p-Qa-1(HLA-E)-NP-mediated binding and expansion of CD8 Treg in vivo, in some embodiments, at least 4 units, at least 5, at least 6, at least 7, at least 8, at least 9 or at least 10 units of the HLA-E-peptide complex are linked together to form a moiety and the moiety is then linked to the surface of the nanoparticle. In some embodiments, the HLA-E-peptide complex comprises biotin, and the complexes are linked together through biotin-avidin interaction to form the moiety. The moiety is conjugated to the carboxyl groups on the NP surface using carbodiimide coupling chemistry (EDC/NHS) to generate p-Qa-1 (HLA-E)-NP particles.

In some embodiments, the HLA-E-peptide complex or the moiety is linked to the surface of the nanoparticle via PEGylation. PEGylation of NP helps prevent internalization of p-Qa-1-NP by phagocytes. Covalent attachment of p-Qa-1(HLA-E) to the distal end of individual PEG molecules rather than to the NP core enables efficient exposure to TCR on CD8+ cells. Alternatively, low molecular-weight chitosan (LMWC) can be adopted as an alternative surface coating method. LMWC also provides hydrophilic layers on NP surface similar to PEG, reducing opsonization and phagocytic uptake of PLGA-LMWC by macrophages (Amoozgar Z. Mol Pharm 2012, Mochizuki M. FASEB 2003).

The NP can be synthesized using any biocompatible polymer, including but not limited to, poly(lactic-co-glycolic acid) (PLGA), poly(ethylene glycol) (PEG), chitosan, and chitosan-PEG. In some embodiments. PLGA is employed to synthesize the NP for the delivery of p-Qa-1 (HLA-E). PLGA is an FDA approved drug delivery reagent and displays favorable features among other available NP particles (Fe3O4-PEG. Quantum dots, or Liposomes), including controllable biodegradability, excellent biocompatibility, and high safety. PLGA-b-PEG copolymers can be synthesized by direct conjugation of PLGA-COOH with NH2-PEG-COOH, as described by Cheng et al. (Formulation of functionalized PLGA-PEG nanoparticles for in vivo targeted drug delivery. *Biomaterials* 28, 869-876 (2007)). The carboxyl group in the copolymer is located at the terminal end of the hydrophilic group allowing availability for surface chemistry.

In some embodiments, the peptide is linked to the HLA-E via a flexible linker. In some embodiments, the heavy chain and light chain (β-2 microglobulin) of the HLA-E are linked via a flexible linker. It is understood and herein contemplated that any linker known by those of skill in the art can be used to make the disclosed NP. The choice of which linker to use can be determined by those of skill in the art based on the desired length and flexibility of the linker. Thus, in some embodiments, the linker can be any short peptide sequence as long as it is hydrophilic and forms a flexible linker by not building a secondary structure that interferes with the main domain structures. In some embodiments, glycine-serine, the most commonly used flexible linker for the production of recombinant single chain protein composed of different moieties, is used. The Gly-Ser linker can be but is not limited to (Gly4Ser)n or (Gly3Ser)n. Thus, for example, the linker can be G4S, (G4S)2, (G4S)3, (G4S) 4. (G4S)5, (G4S)6, (G4S)7, (G4S)8, (G4S)9, (G4S)10, G3S, (G3S)2, (G3S)3, (G3S)4, (G3S)5, (G3S)6, (G3S)7, (G3S)8, (G3S)9, (G3S)10. It is further understood that the linkers used can be a combination of chemical and gly-ser linkers.

For example, the linker between the peptide and the HLA-E can be a chemical linker and the linker between the heavy and light chains of the HLA-E can be a Gly-Ser linker. It is further understood that the for greater flexibility, a longer linker is used; whereas, a shorter linker is used for application where more rigidity is needed. Typically, the linker between the peptide and the HLA-E is 10-20 amino acids long, while the linker between the heavy and light chains of the HLA-E is 15-25 amino acids long. Specifically contemplated herein are NP wherein the linker between the peptide and the β-2 microglobulin of the HLA-E is composed of 15 amino acids [(G4S)3] and β2-microglobulin and the heavy chain of HLA-E is connected by a linker composed of 20 amino acids [(G4S)4].

CD8+ Treg cells depend on IL-15 for activation of suppressive activity. Thus, in some embodiments, a low releasing dose of IL-15 is incorporated into the nanoparticle. The low releasing dose of IL-15 helps promote the expansion of Qa-1(HLA-E)/peptide specific CD8 Treg cells upon stimulation by p-Qa-1(HLA-E). The amino acid sequence of human IL-15 is represented by NCBI Reference Sequence: NP_000576.1 (SEQ ID NO: 3). IL-15 polypeptides also include fragments of IL-15, such as amino acids 49-162 of SEQ ID NO:3, which has previously been characterized as a mature form of IL-15 derived by proteolytic cleavage of a leader sequence from the polypeptide of NP_000576.1, and other fragments that retain the biological activity of IL-15 are encompassed by the term IL-15.

The nanoparticles described herein can be used to treat autoimmune diseases. Accordingly, aspects of the invention involve a method for treating an autoimmune disease by administering to a subject in need of such treatment nanoparticles described herein in an amount effective to ameliorate a symptom of the autoimmune disease. In some embodiments, the peptide in the nanoparticles is $Hsp60_{p216}$. Other aspects of the invention involve a method for treating an autoimmune disease by administering to a subject in need of such treatment a complex comprising a peptide conjugated to any biocompatible polymer, such as, but not limited to poly(lactic-co-glycolic acid) (PLGA), poly(ethylene glycol) (PEG), chitosan, and chitosan-PEG. In some embodiments, the peptide is $Hsp60_{p216}$. In some embodiments, the complex comprises $Hsp60_{p216}$ conjugated to PEG.

Expansion of CD8+ Treg cells specific for Qa-1(HLA-E)-Qdm or Qa-1(HLA-E)-$Hsp60_{p216}$ in vivo can also be induced by administering dendritic cells pulsed with either peptide. It has been discovered that immunization with $Hsp60_{p216}$-loaded dendritic cells (DC) efficiently inhibits the development of collagen-induced arthritis (CIA). Accordingly, aspects of the invention include a method for treating an autoimmune disease. The method comprises contacting dendritic cells isolated from a subject in need of such treatment with $Hsp60_{p216}$ peptide to generate $Hsp60_{p216}$-loaded dendritic cells; and administering to the subject the Hsp60p216-loaded dendritic cells in an amount effective to ameliorate a symptom of the autoimmune disease.

The term "contacting dendritic cells isolated from a subject in need of such treatment with $Hsp60_{p216}$ peptide" includes any means of contacting including but not limited to, mixing the $Hsp60_{p216}$ peptide and the cells in medium, mixing the $Hsp60_{p216}$ peptide in liposomes with the cells or expressing the $Hsp60_{p216}$ peptide from a recombinant nucleic acid in the cells. In some embodiments, the dendritic cells are contacted with $Hsp60_{p216}$ for 2, 4, 6, 8, 12, 16, 18 or 24 hours to generate $Hsp60_{p216}$-loaded dendritic cells.

The term "$Hsp60_{p216}$-loaded dendritic cell" as used herein refers to a dendritic cell presenting $Hsp60_{p216}$ on its surface in a manner effective to selectively expand CD8+ Treg cells that specifically recognize $Hsp60_{p216}$. The dendritic cell may become loaded with the peptide by directly binding the peptide from the medium on its surface or by processing the peptide intra-cytoplasmically before presenting the peptide. Processing the peptide may include proteolytically generating the presented peptide from a longer peptide.

Some aspects of the invention involve a method for treating an autoimmune disease comprising isolating from a subject in need of such treatment CD8+ T cells that bind $Hsp60_{p216}$ peptide; growing the isolated cells in a culture medium containing complexes of IL-15 and IL-15 receptor (IL-15C) until the number of CD8+ T cells that bind Hsp60p216 peptide increases to at least 3-5% of CD8+ T cells, thereby producing a population of cells enriched with CD8+ T cells that bind Hsp60p216 peptide; and administering CD8+ T cells that bind $Hsp60_{p216}$ peptide from the population of cells to the subject in an amount effective to ameliorate a symptom of the autoimmune disease.

Expansion of CD8+ Treg cells specific for Qa-1(HLA-E)-Qdm or Qa-1(HLA-E)-$Hsp60_{p216}$ in vivo can be induced using a moiety comprising at least 4 units of Qa-1(HLA-E)-peptide complex. Accordingly, in some embodiments, the isolating step comprises sorting a sample containing T cells obtained from the subject into CD8+ T cells that bind $Hsp60_{p216}$ peptide using a fluorescently labeled moiety having at least 4 units of a complex, wherein the complex is a major histocompatibility complex (MHC) class I antigen E (HLA-E) linked to $Hsp60_{p216}$ peptide. In some embodiments, the HLA-E-peptide complex comprises biotin, and at least 4 such complexes associate through biotin-avidin interaction to form the moiety. In some embodiments, the avidin is fluorescently labeled. In some embodiments, the avidin is labeled with Phycoerythrin (PE). In some embodiments, the population of cells enriched with CD8+ T cells that bind Hsp60p216 peptide is further enriched using anti-R-Phycoerythrin (PE) microbeads. Specifically. CD8 T cells are first labeled with Qa-1-Hsp60p216 tetramers conjugated with Phycoerythrin (PE). These tetramer positive CD8 cells can then be selected by subsequent labeling with anti-PE antibody conjugated with microbeads and then by mounting them onto the magnetic field. Cells are then collected by detaching from the magnetic field. This procedure enables the enrichment of Tet+ CD8 T cells from the CD8+ T cell pool.

A subject in need of treatment of autoimmune disease is a subject identified as having an autoimmune disease, i.e. the subject has been diagnosed by a physician (e.g., using methods well known in the art) as having an autoimmune disease. In some embodiments, the subject in need of treatment is a subject suspected of having or developing an autoimmune disease, such as a subject presenting one or more symptoms indicative of an autoimmune disease. In some embodiments, a subject suspected of having an autoimmune disease may display abnormal titres of autoantibodies. The subject having abnormal titres of autoantibodies may have at least one other symptom of autoimmune disease or may be without other symptoms associated with autoimmune disease. The term "subject in need of treatment" further includes people who once had an autoimmune disease but whose symptoms have ameliorated.

The subject is an animal, typically a mammal. In one aspect, the subject is a dog, a cat, a horse, a sheep, a goat, a cow or a rodent. In important embodiments, the subject is a human.

A self-antigen (or auto-antigen) is a subject's self-produced constituent, against which the subject mounts an undesired immune response. An "autoantibody" is an antibody produced by a subject, which binds to one or more of the subject's own constituents or self-antigens. The term 'autoimmune disease' refers to those disease states and conditions wherein the immune response of the patient is directed against the patient's own constituents resulting in an undesirable and often terribly debilitating condition. As used herein, 'autoimmune disease' is intended to further include autoimmune conditions, syndromes and the like. Example of autoimmune diseases include, but are not limited to systemic lupus erythematosus, chronic graft versus host disease, rheumatoid arthritis, insulin-dependent diabetes mellitus, multiple sclerosis, psoriasis, inflammatory bowel disease, Sjogren's syndrome, Graves disease, Crohn's disease, Waldenstrom's macroglobulinemia, hyperviscosity syndrome, monoclonal gammopathy of undetermined origin, POEMS syndrome, myeloma, macroglobulinemia, and cold agglutinin disease. In some embodiments, the autoimmune disease involves antibodies to a self-antigen and the subject has the antibodies to the self-antigen.

The nanoparticles, Hsp60p216-loaded dendritic cells and the enriched CD8+ T cells that bind Hsp60p216 peptide described herein can also be used to treat human immunodeficiency virus (HIV) infection. CD4+ follicular helper T cells (TFH) are known to serve as the major CD4 T cell compartment for HIV-1 infection, replication, and production (J Exp Med. 2013 Jan. 14; 210(1):143-56). As described herein, the specialized regulatory CD8+ T cells selectively suppress CD4+ follicular helper T cell (TFH) activity through perforin-dependent lysis and elimination by recognition of class Ib major histocompatibility complex (MHC) peptide Qa-1 (mouse homolog of human leukocyte antigen E (HLA-E)) expressed at the surface of TFH cells. It is believed that the CD8+ Treg cells specific for Qa-1(HLA-E)-Hsp60$_{p216}$ target activated. HIV-infected TFH cells which present Hsp60$_{p216}$ on their surface. Thus, CD8+ cells specific for Hsp60$_{p216}$ peptide can be used to eliminate the TFH cells that serve as major reservoirs for HIV-1 infection. It is believed that the CD8+ Treg cells specific for Qa-1 (HLA-E)-Hsp60$_{p216}$ do not generally suppress the immune response, and instead, target activated. HIV-infected CD4+ follicular helper T cells (TFH) that present the Hsp60$_{p216}$ peptide on their surface. Accordingly, aspects of the invention involve methods of treating HIV infection relate to the development of strategies based on in vivo and in vitro expansion and activation of the CD8+ Treg cells for the treatment of HIV infection.

A subject in need of treatment of HIV infection is a subject identified as having HIV infection, i.e. the subject has been diagnosed by a physician (e.g., using methods well known in the art) as having HIV infection. In some embodiments, the subject in need of treatment is a subject suspected of having or developing HIV infection, such as injection drug users who share needles, infants born to mothers with HIV infection who did not receive HIV therapy during pregnancy, people who received blood transfusions or clotting products between 1977 and 1985 (before screening for the virus became standard practice), people who have unprotected sex, especially with people who have other high-risk behaviors, are HIV-positive, or have AIDS. The term "subject in need of treatment" further includes people who were previously diagnosed with HIV infection and have started to present one or more symptoms of HIV infection.

The subject is an animal, typically a mammal. In one aspect, the subject is a dog, a cat, a horse, a sheep, a goat, a cow or a rodent. In important embodiments, the subject is a human.

The nanoparticles, Hsp60p216-loaded dendritic cells and the enriched CD8+ T cells that bind Hsp60p216 peptide described herein are administered in an effective amount to treat autoimmune diseases or HIV infection. An effective amount is a dose sufficient to provide a medically desirable result and can be determined by one of skill in the art using routine methods. In some embodiments, an effective amount is an amount which results in any improvement in the condition being treated. In some embodiments, an effective amount may depend on the type and extent of the autoimmune disease or condition being treated and/or use of one or more additional therapeutic agents. However, one of skill in the art can determine appropriate doses and ranges of therapeutic agents to use, for example based on in vitro and/or in vivo testing and/or other knowledge of compound dosages.

When administered to a subject, effective amounts of the therapeutic agent will depend, of course, on the particular disease being treated; the severity of the disease; individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

In the treatment of autoimmune disease, an effective amount is that amount which slows the progression of the disease, halts the progression of the disease, or reverses the progression of the disease. An effective amount includes that amount necessary to slow, reduce, inhibit, ameliorate or reverse one or more symptoms associated with the autoimmune disease. In some embodiments, such terms refer to a reduction in the swelling of one or more joints or a reduction in the pain, fatigue and/or fever associated with an autoimmune disorder. In some embodiments, such terms refer to a reduction in the levels of circulating autoantibodies associated with the autoimmune disease. In some embodiments, such terms refer to a reduction in a human's PASI score. In some embodiments, such terms refer to an improvement in a human's global assessment score.

In the treatment of HIV infection, an effective amount is that amount which slows the progression of the disease, halts the progression of the disease, or reverses the progression of the infection. An effective amount includes that amount necessary to slow, reduce, inhibit, ameliorate or reverse one or more symptoms associated with the HIV infection.

An effective amount of a compound typically will vary from about 0.001 mg/kg to about 1000 mg/kg in one or more dose administrations, for one or several days (depending of course of the mode of administration and the factors discussed above).

Actual dosage levels of the therapeutic agent can be varied to obtain an amount that is effective to achieve the desired therapeutic response for a particular patient, compositions, and mode of administration. The selected dosage level depends upon the activity of the particular compound, the route of administration, the tissue being treated, and prior medical history of the patient being treated. However, it is within the skill of the art to start doses of the compound at levels lower than required to achieve the desired therapeutic effort and to gradually increase the dosage until the desired effect is achieved.

Pharmaceutical preparations and compounds are administered to a subject by any suitable route. For example, compositions can be administered orally, including sublingually, rectally, parenterally, intracisternally, intravaginally, intraperitoneally, topically and transdermally (as by powders, ointments, or drops), bucally, or nasally. The pharmaceutical preparations of the present invention may include or be diluted into a pharmaceutically-acceptable carrier. The term "pharmaceutically-acceptable carrier" as used herein means one or more compatible fillers, diluents or other such substances, which are suitable for administration to a human or other mammal such as a dog, cat, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company. Easton. Pa.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLE

A small subset of CD8 cells is essential for the maintenance of self-tolerance and plays an important role in the inhibition of autoimmune disease 1. This subset of regulatory T cells recognizes Qa-1-peptide complexes that are upregulated by pathogenic CD4 T cells, resulting in elimination of these cells through perforin-dependent lysis. Development of strategies based on in vivo expansion and activation of CD8+ Treg represents a new avenue of immunotherapy for the treatment of autoimmune diseases.

Antigen Presentation by Qa-1 (HLA-E):

Two major peptides presented by Qa-1 (HLA-E) are Qdm (B7sp in human) and Hsp60p216. Qdm (B7sp) is a peptide derived from the leader sequence of MHC class Ia which can bind to both the TCR and to CD94/NKG2A receptors. The $Hsp60_{p216}$ peptide can efficiently replace Qdm peptides under conditions of cellular activation and stress. A third peptide that is presented by Qa-1 under conditions of defective antigen processing in the endoplasmic reticulum (ERAAP dysfunction) is the highly conserved peptide FL9. Recognition of Qa-1/FL9 by CD8 T cells may serve to eliminate abnormal cells that have defects in antigen presentation. In sum, Qa-1 dependent recognition represents a potential screening system for cells that are stressed or activated, as demonstrated in cases of infection and secondary to cellular defects of peptide processing associated with autoimmunity and cellular transformation.

Qa-1-peptide tetramers have been generated to detect peptides-specific CD8+ T cells. In the case of Qa-1-Qdm tetramers, a Qa-1 protein containing a point mutation (R72A) was used to prevent binding of Qa-1-Qdm to CD94/NKG2A receptors and allow specific detection of CD8+ T cells that express Qa-1 restricted TCR.

Figure 1B:
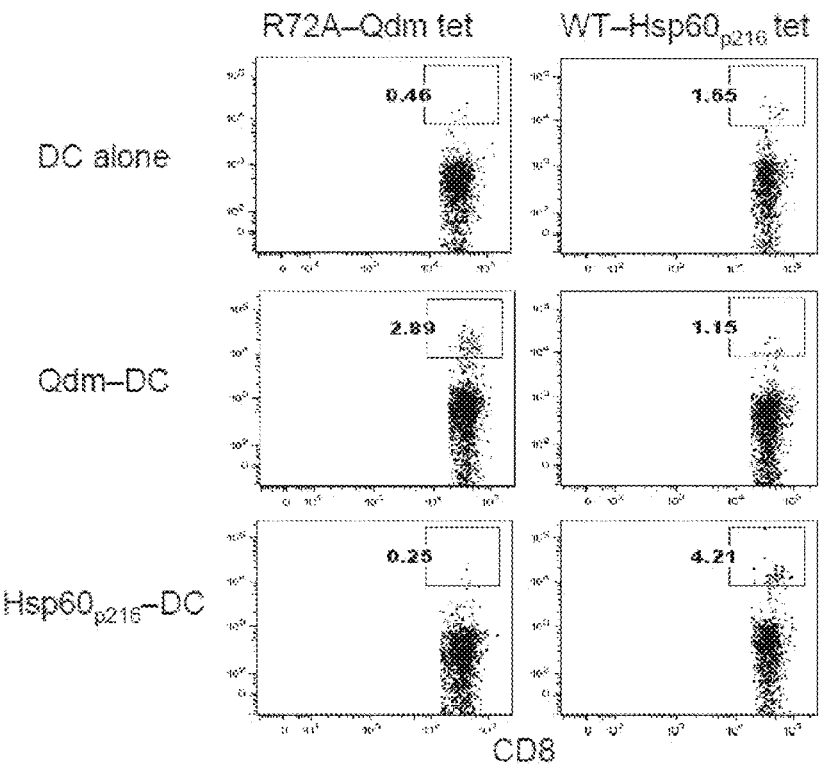
FIG. 1B is a plots showing the selective expansion of Qa-1-restricted CD8 Treg, where CII-immune B6 mice were immunized with $Kb^{-/-}Db^{-/-}$ DC loaded with or without the indicated peptide as described in FIG. 1A. Qdm- or Hsp60p216-CD8 cells from draining lymph nodes were analyzed at d42 by staining with RA.Qa-1-Qdm-tetramer or WT.Qa-1-Hsp60p216-tetramer, respectively. Representative FACS plots are shown.

DC/Peptide Immunization and Inhibition of Autoimmune Disease:

Expansion of CD8 T cells specific for Qa-1-Qdm or Qa-1-$Hsp60_{p216}$ in vivo can be induced by vaccination of mice with dendritic cells pulsed with either peptide. WT B6 mice that were immunized with chicken collagen type II were treated by subcutaneous injection of irradiated B6. $Kb^{-/-}Db^{-/-}$ DC pulsed with either $Hsp60_{p216}$ or Qdm peptides at days 27, 36, and 49 and the progression of arthritis was monitored. Immunization with $Hsp60_{p216}$-loaded DC efficiently inhibits the development of collagen-induced arthritis (CIA), while vaccination with DC pulsed with Qdm peptide does not suppress disease progression (FIG. 1A). Immunization of mice with $Hsp60_{p216}$-loaded $Kb^{-/-}Db^{-/-}$ DC was associated with expansion of Qa-1-$Hsp60_{p216}$-specific CD8+ T reg cells as detected by Qa-1-$Hsp60_{p216}$ tetramers (FIG. 1B). Although immunization with Qdm-loaded $Kb^{-/-}Db^{-/-}$ DC resulted in increased numbers of Qa-1 R72A-Qdm tetramer+ cells (FIG. 1B), this immunization did not inhibit disease (FIG. 1A).

These findings indicate that specific in vivo expansion of Hsp60p216-specific CD8 Treg can contribute to the suppression of pathogenic CD4 cells and inhibition of disease progression, a finding supported by adoptive transfer studies of purified tetramer+ $Hsp60_{p216}$-specific CD8+ T cells as described below.

Figure 2A:
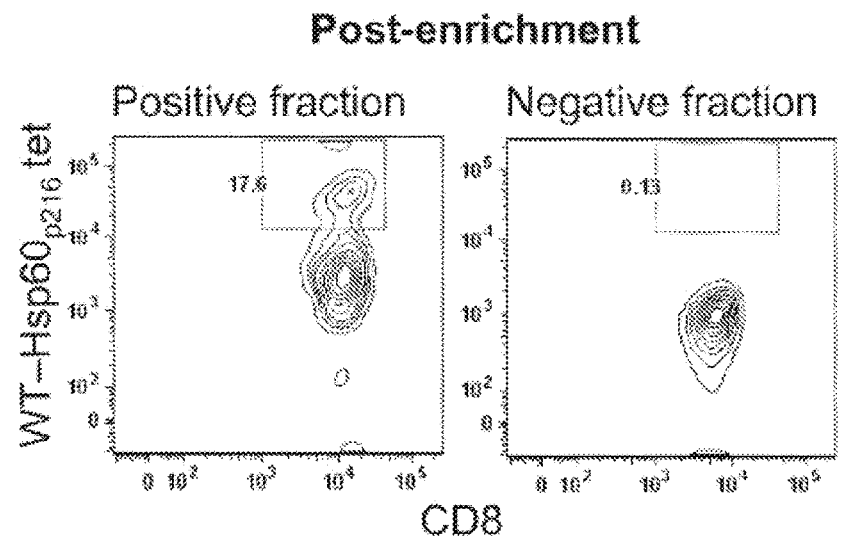
FIG. 2A is a plot showing that selective expansion of Qa-1-restricted CD8+ Treg inhibited arthritis. Hsp60p216-tet+ and Hsp60p216-tet– CD8 cells were sorted from CII-immune B6 mice before incubation in IL-15C (10 ng ml-1)*10d. These cells were then incubated with Hsp60p216 tetramer and enriched by anti-PE microbeads. FACS analysis of tetramer staining of these cells indicated that incubation of CD8 cells that were tet+ but not tet– resulted in a substantial number of Hsp60p216 tet+ cells.
Figure 2B:
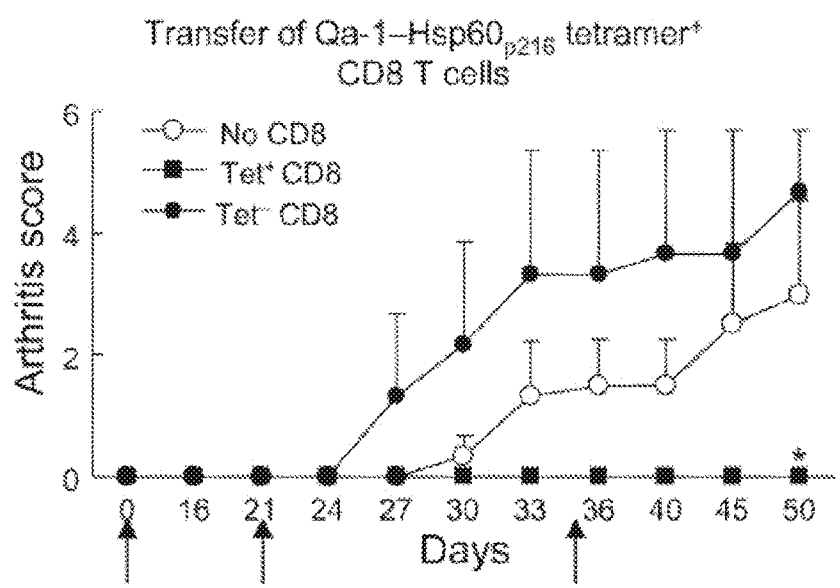
FIG. 2B is a graph showing the transfer of Qa-1-$Hsp60_{p216}$ tetramer$^+$ CD8 T cells. The Hsp60p216-tet+ or Hsp60p216-tet– fraction of CD8 cells was transferred into $Rag2^{-/-}$-$Prf1^{-/-}$ mice along with CD4 and B cells from arthritic mice. Arthritis was induced as described in Methods. Arthritis scores are shown; 3 mice per group.
Figure 2C:
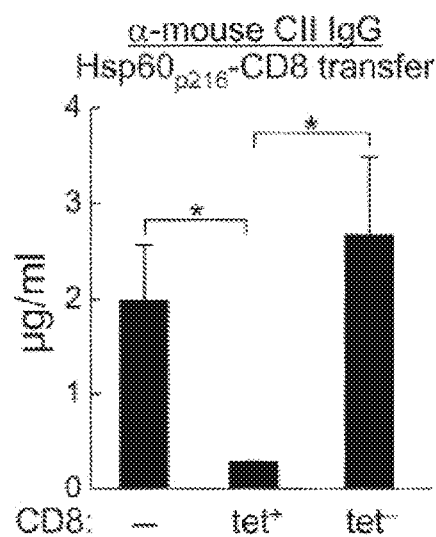
FIG. 2C is a bar graph showing anti-mouse CII IgG titers at d30; 3 mice per group. Group (tet– CD8) versus group (tet+ CD8), *P<0.05.
Figure 2D:
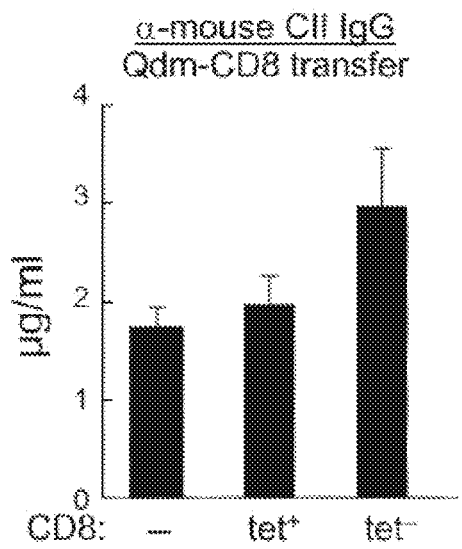
FIG. 2D is a bar graph showing anti-mouse CII IgG titers at d30. Here Qdm-tet+ or Qdm-tet− CD8 cells were transferred into Rag2$^{-/-}$Prf1$^{-/-}$ mice along with CD4 and B cells from arthritic mice.
Figures 2E, 3:
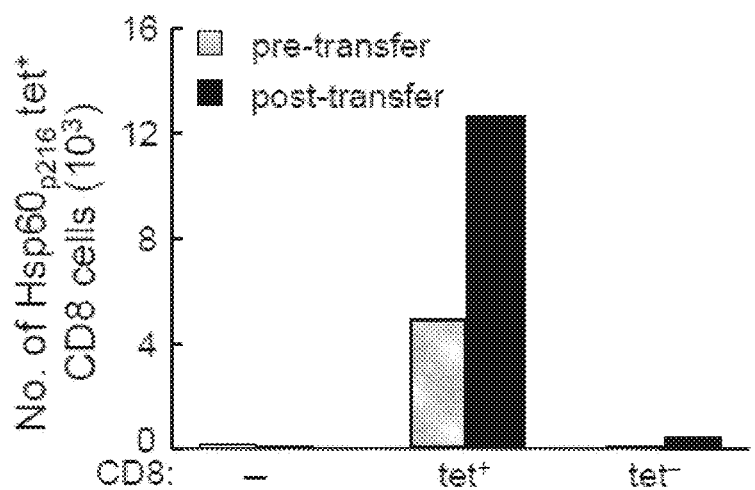
FIG. 2E is a bar graph showing selective expansion of Qa-1-restricted CD8 Treg. Hsp60p216-tet+ CD8 cells were enumerated at d34 after adoptive transfer as described in FIG. 2B.
FIG. 3 shows the amino acid sequence of human IL-15 (SEQ ID NO: 3; NCBI Reference Sequence: NP_000576.1).

Inhibition of Autoimmune Disease by Qa-1-Hsp60p216 Tetramer+ CD8 Cells:

To test the ability of $Hsp60_{p216}$-Qa-1-restricted CD8 cells to carry CD8+ T reg activity. Qa-1-$Hsp60_{p216}$-tetramer+ CD8 T cells were separated from the tetramer-fraction by consecutive FACS sorting and microbead selection (FIG. 2A). Adoptive transfer of enriched Qa-1-$Hsp60_{216}$-tetramer+ CD8 cells ($3.5 \times 10^4$ cells), but not Qa-1-$Hsp60_{p216}$-tetramer- CD8 cells into Rag2-/-Prf1-/- hosts along with CII-immune CD4 and B cells inhibited autoantibody production and halted arthritis progression (FIG. 2B-D). Analysis of CD8 cells in these adoptive hosts revealed an expanded population of Qa-1-$Hsp60_{p216}$-tetramer+ CD8 cells after transfer of tetramer+ but not after transfer of tetramer- CD8 cells (FIG. 2E). In contrast, transfer of R72A Qa-1-Qdm tetramer+ CD8+ cells did not prevent disease progression, consistent with the failure of Qdm-DC immunization to inhibit disease progression.

Effects of p-HLA-E-NP Vaccination in Humanized Mice:

Expansion of HLA-E/peptide specific CD8 cells by p-HLA-E-NP vaccination is tested in NOD.Cg-$B2m^{tm1Unc}Prkdc^{scid}Il2^{tm1Wjl}$/SzJ (NSB) mice expressing the HLA-E transgene (NSB-HLA-E) covalently linked to hβ2m using HLA-E/peptide tetramers.

Humanized NSB-HLA-E mice that are reconstituted with human immune cells and vaccinated with p-HLA-E-NP are tested for the frequency of peptide specific human CD8 cells and their surface phenotype (CD45RO and KIR). Monitoring of the expansion of HLA-E/$HSP_{p216}$ specific CD8 T cells by detecting these cells using tetramers in humanized mice can be extended to detection of Tetramer⁺ CD8 cells in PBMC of patients.

Superior Feature of p-Qa-1 (HLA-E)-NP Vaccination:

Both Qa-1 in mice and HLA-E in men exhibit a limited polymorphism distinct from MHC class Ia molecules that are highly polymorphic. The human HLA-E gene, for example, is expressed one out of two alleles which differ at a single amino acid. Therefore, a generalized immunotherapy using p-Qa-1 (HLA-E)-NP-based vaccination for the treatment of autoimmune disease represents a promising therapeutic strategy that does not depend on extensive individualized pMHC-NP design.

Qa-1 R72A-Qdm and Qa-1-Hsp60$_{p216}$ tetramers were designed to detect CD8+ T cells specific for Qa-1-Qdm or Qa-1-Hsp60$_{p216}$. The tetramers were used to enrich CD8 cells specific for these ligands and the cells were tested for regulatory activity in the context of CIA. Vaccination of mice with dendritic cells (DC) pulsed with defined peptides, resulted in expansion of CD8$^+$ T cells specific for Qa-1-Qdm or Qa-1-Hsp60$_{p216}$ in vivo. Although immunization with Hsp60$_{216}$-loaded DC efficiently inhibited the development of CIA, vaccination with DC pulsed with Qdm peptide did not suppress disease progression. Moreover, transfer of a small number of Qa-1-Hsp60p216 tetramer$^+$ CD8+ cells, but not R72A Qa-1-Qdm tetramer$^+$ CD8+ cells, inhibited disease progression. Altered processing of MHC class Ia leader peptide in activated cells or stressed cells results in increased processing and presentation of alternate peptides, including those derived from Hsp60, to Qa-1-restricted CD8$^+$ T cells. Inhibitory signaling associated with the interaction between the CD94/NKG2A receptor and the Qa-1-Qdm complex overrides TCR-dependent activation by Qa-1-Qdm ligands.

In sum, amelioration of autoimmune arthritis may be achieved by targeting arthrogenic T$_{FH}$ and T$_H$17 cells through mobilization of CD8$^+$ Treg. CD8+ Treg infusion may be used for patients who develop resistance to MTX treatment or relapse after MTX withdrawal. Moreover, the IL-15 dependence of CD8$^+$ Treg may be exploited for development of personalized CD8+ Treg-based cellular therapy to arthritis after in vitro expansion, or direct peptide-based expansion of CD8$^+$ Treg in vivo. The development of strategies based on specific expansion and activation of CD8$^+$ Treg represents a new and potentially effective approach to the treatment of autoimmune disease.

This invention is not limited in its application to the details of construction and the arrangement of components set forth in the above description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

REFERENCES

Anderton, S. M., Radu, C. G., Lowrey, P. A., Ward, E. S., and Wraith, D. C. (2001). Negative selection during the peripheral immune response to antigen. J Exp. Med. 193, 1-11.

Anfossi, N., Pascal, V., Vivier, E., and Ugolini, S. (2001). Biology of T memory type 1 cells. Immunol. Rev. 181, 269-278.

Anfossi, N., Robbins, S. H., Ugolini, S., Georgel, P., Hoebe, K., Bouneaud, C., Ronet, C., Kaser, A., DiCioccio, C. B., Tomasello, E., Blumberg, R. S., Beutler, B., Reiner, S. L., Alexopoulou, L., Lantz, O., Raulet, D. H., Brossay, L., and Vivier, E. (2004). Expansion and function of CD8+ T cells expressing Ly49 inhibitory receptors specific for MHC class I molecules. J. Immunol. 173, 3773-3782.

Bouneaud, C., Kourilsky, P., and Bousso, P. (2000). Impact of negative selection on the 'I' cell repertoire reactive to a self-peptide: a large fraction of T cell clones escapes clonal deletion. Immunity 13, 829-840.

Buhier, J. A., Bennett, S. M., Sproule, T. J., Lyons, B. L., Olland, S., Young, D. A., and Roopenian, D. C. (2007). Treatment of BXSB-Yaa mice with IL-21R-Fc fusion protein minimally attenuates systemic lupus erythematosus. Ann. N. Y. Acad. Sci. 1110, 590-601.

Chwae, Y. J., Chang, M. J., Park, S. M., Yoon, H., Park, H. J., Kim, S. J., and Kim, J. (2002). Molecular mechanism of the activation-induced cell death inhibition mediated by a p70 inhibitory killer cell Ig-like receptor in Jurkat T cells. J. Immunol. 169, 3726-3735.

Coles, M. C., McMahon, C. W., Takizawa, H., and Raulet, D. H. (2000). Memory CD8 'I' lymphocytes express inhibitory MHC-specific Ly49 receptors. Eur. J. Immunol. 30, 236-244.

Davies, A., Kalb, S., Liang, B., Aldrich, C. J., Lemonnier, F. A., Jiang, H., Cotter, R., and Soloski, M. J. (2003). A peptide from heat shock protein 60 is the dominant peptide bound to Qa-1 in the absence of the MHC class Ia leader sequence peptide Qdm. J. Immunol. 170, 5027-5033.

Gati, A., Guerra, N., Gaudin, C., Da Rocha, S., Escudier, B., Lecluse, Y., Bettaieb, A., Chouaib, S., and Caignard, A. (2003). CD158 receptor controls cytotoxic T-lymphocyte susceptibility to tumor-mediated activation-induced cell death by interfering with Fas signaling. Cancer Res. 63, 7475-7482.

Goldrath, A. W. and Bevan, M. J. (1999). Selecting and maintaining a diverse T-cell repertoire. Nature 402, 255-262.

Izui, S., Higaki, M., Morrow, D., and Merino, R. (1988). The Y chromosome from autoimmune BXSB/MpJ mice induces a lupus-like syndrome in (NZW x C57BUJ6)F1 male mice, but not in C57BL/6 male mice. Eur. J. Immunol. 18, 911-915.

Jiang, H., Curran, S., Ruiz-Vazquez, E., Liang, B., Winchester, R., and Chess, L. (2003). Regulatory CD8+ T cells fine-tune the myelin basic protein-reactive T cell receptor V beta repertoire during experimental autoimmune encephalomyelitis. Proc. Natl. Acad. Sci. U.S.A 100, 8378-8383.

Judge, A. D., Zhang, X., Fujii, H., Surh, C. D., and SprentJ. (2002). Interleukin 15 controls both proliferation and survival of a subset of memory-phenotype CD8(+) T cells. J. Exp. Med. 196, 935-946.

Kearney, E. R., Pape, K. A., Loh, D. Y., and Jenkins, M. K. (1994). Visualization of peptide-specific T cell immunity and peripheral tolerance induction in vivo. Immunity 1(4), 327-339.

Kikuchi, S., Fossati-Jimack, L., Moll, T., Amano, H., Amano, E., Ida, A., IThnou-Zekri, N., Laporte, C., Santiago-Raber, M. L., Rozzo, S. J., Kotzin, B. L., and Izui, S. (2005). Differential role of three major New Zealand Black-derived loci linked with Yaa-induced murine lupus nephritis. J. Immunol. 174, 1111-1117.

Kim, H. J., Verbinnen, B., Tang, X., Lu, L., and Cantor, H. (2010). Inhibition of follicular T helper cells by CD8+ Treg is essential for self tolerance. Nature 467, 328-332.

Leavenworth J. W., Wang, X., Wenander, C. S., Spee, P. & Cantor, H. Mobilization of natural killer cells inhibits development of collagen-induced arthritis. Proc Natl Acad Sci USA 108, 14584-14589 (2011).

Leavenworth J. W. et al. Analysis of the cellular mechanism underlying inhibition of EAE after treatment with anti-NKG2A F(ab')2. Proc. Natl. Acad. Sci. U.S.A 107, 2562-2567 (2010).

Littman, D. R. and Rudensky, A. Y. (2010). Th17 and regulatory T cells in mediating and restraining inflammation. Cell 140, 845-858.

Lo, W. F., Ong, H., Metcalf, E. S., and Soloski, M. J. (1999). T cell responses to gram-negative intracellular bacterial pathogens: a role for CD8+ T cells in immunity to *Salmonella* infection and the involvement of MHC class Ib molecules. J. Immunol. 162, 5398-5406.

Lo, W. F., Woods, A. S., DeCloux, A., Cotter, R. J., Metcalf, E. S., and Soloski, M. J. (2000). Molecular mimicry mediated by MHC class Ib molecules after infection with gram-negative pathogens. Nat. Med. 6, 215-218.

Lu, L., Kim, H. J., Werneck, M. B., and Cantor, H. (2008). Regulation of CD8+ regulatory T cells: Interruption of the NKG2A-Qa-1 interaction allows robust suppressive activity and resolution of autoimmune disease. Proc. Natl. Acad. Sci. U.S.A 105, 19420-19425 (2008).

Martin, D. A., Zheng, L., Siegel, R. M., Huang, B., Fisher, G. H., Wang, J., Jackson, C. E., Puck, J. M., DaleJ., Straus, S. E., Peter, M. E., Krammer, P. H., Fesik, S., and Lenardo, M. J. (1999). Defective CD95/APO-1/Fas signal complex formation in the human autoimmune lymphoproliferative syndrome, type Ia. Proc. Natl. Acad. Sci. U.S.A. 96, 4552-4557.

Mestas, J. and Hughes, C. C. (2004). Of mice and not men: differences between mouse and human immunology. J. Immunol. 172, 2731-2738.

Mingari, M. C., Schiavetti, F., Ponte, M., Vitale, C., Maggi, E., Romagnani, S., Demarest, J., Pantaleo, G., Fauci, A. S., and Moretta, L. (1996). Human CD8+ T lymphocyte subsets that express HLA class I-specific inhibitory receptors represent oligoclonally or monoclonally expanded cell populations. Proc. Natl. Acad. Sci. U.S.A 93, 12433-12438.

Morel, L., Croker, B. P., Blenman, K. R., Mohan, C., Huang, G., Gilkeson, G., and Wakeland, E. K. (2000). Genetic reconstitution of systemic lupus erythematosus immunopathology with polycongenic murine strains. Proc. Natl. Acad. Sci. U.S.A 97, 6670-6675.

Moretta, L., Romagnani, C., Pietra, G., Moretta, A., and Mingari, M. C. (2003). NK-CTLs, a novel HLA-E-restricted T-cell subset. Trends Immunol. 24, 136-143.

Moser, J. M., GibbsJ., Jensen, P. E., and Lukacher, A. E. (2002). CD94-NKG2A receptors regulate antiviral CD8 (+) T cell responses. Nat. Immunol. 3, 189-195.

Panoutsakopoulou, V., Sanchirico, M. E., Huster, K. M., Jansson, M., Granucci, F., Shim, D. J., Wucherpfennig, K. W., and Cantor, H. (2001). Analysis of the Relationship between Viral Infection and Autoimmune Disease. Immunity 15, 137-147.

Pietra, G., Romagnani, C., Falco, M., Vitale, M., Castriconi, R., Pende, D., Millo, E., Anfossi, S., Biassoni, R., Moretta, L., and Mingari, M. C. (2001). The analysis of the natural killer-like activity of human cytolytic T lymphocytes revealed HLA-E as a novel target for TCR alpha/beta-mediated recognition. Eur. J. Immunol. 31, 3687-3693.

Pisitkun, P., Deane, J. A., Difilippantonio, M. J., Tarasenko, T., Satterthwaite, A. B., and Bolland, S. (2006). Autoreactive B cell responses to RNA-related antigens due to TLR7 gene duplication. Science 312, 1669-1672.

Roger, J., Chalifour, A., Lemieux, S., and Duplay, P. (2001). Cutting edge: Ly49A inhibits TCR/CD3-induced apoptosis and IL-2 secretion. J. Immunol. 167, 6-10.

Slifka, M. K., Blattman, J. N., Sourdive, D. J., Liu, F., Huffman, D. L., Wolfe, T., Hughes, A., Oldstone, M. B., Ahmed, R., and von Herrath, M. G. (2003). Preferential escape of subdominant CD8+ T cells during negative selection results in an altered antiviral T cell hierarchy. J. Immunol. 170, 1231-1239.

Soloski, M. J., DeClou, A., Aldrich, C. J., and Forman, J. (1995). Structural and functional characteristics of the class IB molecule, Qa-1. Immunol. Rev. 147, 67-89.

Speiser, D. E., Pittet, M. J., Valmori, D., Dunbar, R., Rimoldi, D., Lienard, D., MacDonald, H. R., Cerottini, J. C., Cerundolo, V., and Romero, P. (1999). In vivo expression of natural killer cell inhibitory receptors by human melanoma-specific cytolytic T lymphocytes. J. Exp. Med. 190, 775-782.

Subramanian, S., Tus, K., Li, Q. Z., Wang, A., Tian, X. H., Zhou, J., Liang, C., Bartov, G., McDaniel, L. D., Zhou, X. J., Schultz, R. A., and Wakeland, E. K. (2006). A Tlr7 translocation accelerates systemic autoimmunity in murine lupus. Proc. Natl. Acad. Sci. U.S.A 103, 9970-9975.

Sullivan, B. A., Kraj, P., Weber, D. A., Ignatowicz, L., and Jensen, P. E. (2002). Positive selection of a Qa-1-restricted T cell receptor with specificity for insulin. Immunity 17, 95-105.

Tompkins, S. M., Kraft, J. R., Dao, C. T., Soloski, M. J., and Jensen, P. E. (1998). Transporters associated with antigen processing (TAP)—independent presentation of soluble insulin to alpha/beta T cells by the class Ib gene product, Qa-1(b). J. Exp. Med. 188, 961-971.

Transy, C., Nash, S. R., David-Watine, B., Cochet, M., Hunt, S. W., Hood, L. E., and Kourilsky, P. (1987). A low polymorphic mouse H-2 class I gene from the Tla complex is expressed in a broad variety of cell types. J. Exp. Med. 166, 341-361.

Ugolini, S., Arpin, C., Anfossi, N., Walzer, T., Cambiaggi, A., Forster, R., Lipp, M., Toes, R. E., Melief, C. J., Marvel J., and Vivier, E. (2001). Involvement of inhibitory NKRs in the survival of a subset of memory-phenotype CD8+ T cells. Nat. Immunol. 2, 430-435.

Vivier, E. and Anfossi, N. (2004). Inhibitory NK-cell receptors on T cells: witness of the past, actors of the future. Nat. Rev. Immunol 4, 190-198.

Young, N. T., Uhrberg, M., Phillips, J. H., Lanier, L. L., and Parham, P. (2001). Differential expression of leukocyte receptor complex-encoded Ig-like receptors correlates with the transition from effector to memory CTL. J. Immunol. 166, 3933-3941.

Zeng, R., Spolski, R., Finkelstein, S. E., Oh, S., Kovanen, P. E., Hinrichs, C. S., Pise-Masison, C. A., Radonovich, M. F., Brady, J. N., Restifo, N. P., Berzofsky, J. A., and Leonard, W. J. (2005). Synergy of IL-21 and IL-15 in regulating CD8+ T cell expansion and function. J. Exp. Med. 201, 139-148.

What is claimed is:

1. A method for treating an autoimmune disease comprising:
   administering to a subject in need of such treatment a nanoparticle comprising a biocompatible polymer and a complex in an amount effective to ameliorate a symptom of the autoimmune disease,
   wherein the complex is a major histocompatibility complex (MHC) class 1 antigen E (HLAE) linked to a peptide,
   wherein the HLA-E peptide complex is linked to the surface of the nanoparticle, and
   wherein the peptide comprises $Hsp60_{p216}$ or FL9.

2. The method of claim 1, wherein the autoimmune disease is selected from the group consisting of systemic lupus erythematosus, chronic graft versus host disease, rheumatoid arthritis, insulin-dependent diabetes mellitus, multiple sclerosis, psoriasis, inflammatory bowel disease, Sjogren's syndrome, Graves disease, Crohn's disease, Waldenstrom's macroglobulinemia, hyperviscosity syndrome, monoclonal gammopathy of undetermined origin, POEMS syndrome, myeloma, macroglobulinemia, and cold agglutinin disease.

3. The method of claim 1, wherein at least 4 units, at least 5, at least 6, at least 7, at least 8, at least 9 or at least 10 units of the HLA-E-peptide complex are linked together to form a moiety and the moiety is linked to the surface of the nanoparticle.

4. The method of claim 3, wherein the HLA-E-peptide complex comprises biotin, and the complexes are linked together through biotin-avidin interaction to form the moiety.

5. The method of claim 3, wherein the HLA-E-peptide complex or the moiety is linked to the surface of the nanoparticle via PEGylation.

6. The method of claim 1, wherein the peptide is linked to the HLA-E via a flexible linker.

7. The method of claim 6, wherein the flexible linker is a Gly-Ser linker.

8. The method of claim 7, wherein the Gly-Ser linker is $(Gly_4Ser)_n$ or $(Gly_3Ser)_n$, and n is 1, 2, 3, 4, 5, 6, 7, 8, 9, or 10.

9. The method of claim 1, wherein the heavy chain and light chain (β-2 microglobulin) of the HLA-E are linked via a flexible linker.

10. The method of claim 9, wherein the flexible linker is a Gly-Ser linker.

11. The method of claim 10, wherein the Gly-Ser linker is $(Gly_4Ser)_n$ or $(Gly_3Ser)_n$, and n is 1, 2, 3, 4, 5, 6, 7, 8, 9, or 10.

12. The method of claim 1, wherein the peptide is linked to the HLA-E via a first flexible linker, and the heavy chain and light chain (β-2 microglobulin) of the HLA-E are linked via a second flexible linker, wherein the first flexible linker is $(Gly_4Ser)_3$ and the second flexible linker is $(Gly_4Ser)_4$.

13. The method of claim 1, wherein the polymer is selected from the group consisting of poly(lactic-co-glycolic acid) (PLGA), poly(ethylene glycol) (PEG), chitosan, and chitosan-PEG.

14. The method of claim 1, wherein a low releasing dose of IL-15 is incorporated into the nanoparticle.

15. The method of claim 1, wherein the polymer is poly(ethylene glycol) (PEG).

* * * * *

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence

```
<220> FEATURE:
<223> OTHER INFORMATION: Synthetic polypeptide

<400> SEQUENCE: 1

Gly Met Lys Phe Asp Arg Gly Tyr Ile
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 2

Phe Tyr Ala Glu Ala Thr Pro Met Leu
1               5

<210> SEQ ID NO 3
<211> LENGTH: 162
<212> TYPE: PRT
<213> ORGANISM: Artificial Sequence
<220> FEATURE:
<223> OTHER INFORMATION: Synthetic polypeptide

<400> SEQUENCE: 3

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```